US006495586B2

(12) United States Patent
Jacobs et al.

(10) Patent No.: US 6,495,586 B2
(45) Date of Patent: Dec. 17, 2002

(54) SCYTONEMIN AND METHODS OF USING THEREOF

(75) Inventors: Robert S. Jacobs, Santa Barbara, CA (US); Lisa A. Marshall, Collegeville, PA (US); William H. Gerwick, Corvallis, OR (US); Christopher Stevenson, King of Prussia, PA (US)

(73) Assignees: The Regents of the University of California, Oakland, CA (US); Oregon State University, Corvallis, OR (US); GlaxoSmithKline, King of Prussia, PA (US)

( * ) Notice: Subject to any disclaimer, the term of this patent is extended or adjusted under 35 U.S.C. 154(b) by 0 days.

(21) Appl. No.: 09/790,640

(22) Filed: Feb. 23, 2001

(65) Prior Publication Data

US 2001/0041731 A1 Nov. 15, 2001

Related U.S. Application Data

(60) Provisional application No. 60/185,029, filed on Feb. 25, 2000.

(51) Int. Cl.$^7$ .............................................. A61K 31/40
(52) U.S. Cl. ....................................................... 514/411
(58) Field of Search ......................................... 514/411

(56) References Cited

U.S. PATENT DOCUMENTS

| 5,461,070 A | * 10/1995 | Gerwick et al. | ............ 514/411 |
| 5,498,405 A | 3/1996 | Gerwick et al. | .............. 424/59 |
| 5,508,026 A | 4/1996 | Gerwick et al. | .............. 424/59 |
| 6,020,194 A | 2/2000 | Muller et al. | ................ 435/325 |
| 6,043,030 A | 3/2000 | Beach et al. | .................... 435/6 |
| 6,214,456 B1 | 4/2001 | Weng et al. | ................. 435/7.1 |

OTHER PUBLICATIONS

Stein, Editor–in–Chief, Internal Medicine, 4$^{TH}$ Edition, Chapters 71 and 72, copyright 1994.*
Atherton–Fessler, S., et al. Mechanisms of p34$^{cdc2}$ Regulation. *Molec. Cell. Biol.* (1993) 13(3):1675–1685.
Butler, D. M., et al. Stimulation of Human Synovial Fibroblast DNA Synthesis by Recombinant Human Cytokines. *J. of Rheumatology* (1988) 15:1463–1470.
Clay, F. J., et al. Identification and Cloning of a Protein Kinase–Encoding Mouse Gene Plk, Related to the Polo Gene of Drosophila. *PNAS USA* (1993) 90:4882–4886.
De Bondt, H. L., et al. Crystal Structure of Cyclin–Dependent Kinase 2. *Nature* (1993) 363:595–602.
Desai, D., et al. Activation of Human Cyclin–Dependent Kinases In Vitro. *Molec. Biol. Cell* (1992) 3:571–582.
Ducommun, B., et al. Cdc2 Phosphorylation is Required for its Interaction with Cyclin. *EMBO J.* (1991) 10(11):3311–3319.
Dunphy, W. G., and Kumagai, A. The cdc25 Protein Contains an Intrinsic Phosphatase Activity. *Cell* (1991) 67:189–196.

Endicott, J. A., et al. Mutational Analysis Supports a Structural Model for the Cell Cycle protein Kinase p34. *Prot. Eng.* (1994) 7(2):243–253.
Folkman, J. and Haudenschild, C. Angiogenesis in vitro. *Nature* 288:551–556, 1993.
Golsteyn, R. M. et al. The Family of Polo–like Kinases. *Progress in Cell Cycle Research* (1996) 2:107–114.
Golsteyn, R. M., et al. Cell Cycle Analysis and Chromosomal Localization of Human Plk1, a Putative Homologue of the Mitotic Kinases Drosophila polo and *Saccharomyces cerevisiae* Cdc5. *J. of Cell Science* (1994) 107:1509–1517.
Graham, T. M., et al. Characterisation of a Polo–like Protein Kinase Gene Homologue from an Evolutionary Divergent Eukaryote, *Trypanosoma brucei*. Gene (1998) 207:71–77.
Hamanaka, R., et al. Cloning and Characterization of Human and Murine Homologues of the *Drosophila polo* Serine–Threonine Kinase. *Cell Growth and Differentiation* (1994) 5:249–257.
Huang, L., et al. GRB2 and SH–PTP2: Potentially Important Endothelial Signalling Molecules Downstream of the TEK/TIE2 Receptor Tyrosine Kinase. Oncogene (1995) 11:2097–2103.
Jackson, J. R., et al. An Indolocarbazole Inhibitor of Human Checkpoint Kinase (Chk1) Abrogates Cell Cycle Arrest Caused by DNA Damage. *Cancer Research* 60:566–572, Feb., 2000.
Jeffrey, P. D., et al. Mechanism of CDK Activation Revealed by the Structure of a CyclinA–CDK2 Complex. *Nature* (1995) 376:313–320.
Kitada, K., et al. A Multicopy Suppressor Gene of the *Saccharomyces cervisiae* G1 Cell Cycle Mutant Gene dbf4 Endoces a Protein Kinase and is Identified as CDC5. *Molec. Cell Biol.* (1993) 13(7):44445–4457.
Kumagai, A., et al. Purification and Molecular Cloning of PIx1, a Cdc25–Regulatory Kinase from Xenopus Egg Extracts. *Science* (1996) 273:1377–1380.
Lane, H. A., et al., Antibody Microinjection Reveals an Essential Role for Human Polo–like Kinase 1 (Plk1) in the Functional Maturation of Mitotic Centrosomes. *J. Cell Biol* (1996)135(6/2):1701–1713.
Llamazares, S., et al. Polo Gene Encodes a Protein Kinase Homolog Required for Mitosis in Drosophila. *Genes & Devel.* (1991) 5:2153–2165.
Maller, J. L. Mitotic Control. *Curr. Opin. In Cell Biol.* (1991) 3:269–275.

(List continued on next page.)

Primary Examiner—Dwayne C. Jones
(74) Attorney, Agent, or Firm—Suzannah K. Sundby; Jacobson Holman PLLC

(57) ABSTRACT

Disclosed are compounds having a scytoneman skeleton, such as scytonemin, and methods of using thereof. Methods of using a compound having a scytoneman skeleton to inhibit, modulate, attenuate, or prevent cell-cycle progression, cell proliferation, kinase activity, or induce apoptosis are disclosed. Also disclosed are methods of treating, preventing, or inhibiting diseases and disorders associated with cell cycle progression, cell proliferation, kinase activity, tissue hyperplasia or angiogenesis, such as cancer or an inflammatory disease.

17 Claims, 10 Drawing Sheets

OTHER PUBLICATIONS

Nasmyth, K. Control of the Yeast Cell Cycle by the Cdc28 Protein Kinase. *Curr. Opin. In Cell Biol.* (1993) 5:166–179.

Nigg, E. A. Polo–like Kinases: Positive Regulators of Cell Division from Start to Finish. *Curr. Opin. In Cell Biol.* (1998) 10:776–783.

Norbury, C., et al. Regulatory Phosphorylation of the $p34^{cdc2}$ Protein Kinase in Vertebrates. *EMBO J.* (1991) 10(11):3321–3329.

Norbury, C. and Nurse, P. Animal Cell Cycles and Their Control. *Annu. Rev. Biochem.* (1992) 61:441–470.

Ohkura, H., et al. *The Conserved chizosaccharomyces pombe* Kinase plo1, Required to Form a Biopolar Spindle, the Actin Ring, and Septum, Can Drive Septum Formation in G1 and G2 Cells. *Genes & Devel.* (1995) 9:1059–1073.

Remmers, E. F., et al. Platelet–Derived Growth Factor and Heparin–Binding (Fibroblast) Growth Factors in the Synovial Tissue Pathology of Rheumatoid Arthritis. *Seminars in Arthritis and Rheumatism* (1991) 21(3):191–199.

Rubin, K., et al. Expression of Platelet–Derived Growth Factor Receptors is Induced on Connective Tissue Cells During Chronic Synovial Inflammation. *Scand. J. Immunol.* (1988) 27:285–294.

Roshak, A. K., et al. The Human Polo–like Kinase. PLK, Regulates cdc2/cyclin B Through Phosphorylation and activation of the cdc25C Phosphatase. *Cellular Signalling* (2000) 12:405–411.

Sherr, C. J. Mammalian G1 Cyclins. *Cell* (1993) 73:1059–1065.

Smith, M. R., et al. Malignant Transformation of Mammalian Cells Initiated by Constitutive Expression of the Polo––like Kinase. *Biochem. and Biophys. Research Comm.* (1997) 234:397–405.

Sunkel, C. E. and Glover, D. M. *Polo*, a Mitotic Mutant of Drosophila Displaying Abnormal Spindle Poles. *J. of Cell Science* (1988) 89:25–38.

* cited by examiner

Figure 7

| Protein Kinase | Kinase Type | IC50 of SCY Inhibition |
|---|---|---|
| GST-Tie2 | Tyrosine | > 10 µM |
| PKA | Serine/Threonine | > 10 µM |
| rh - PKCβ2 | Serine/Threonine | 2.73 ± 0.35 µM |
| rh - CDK1/cyclin B | Serine/Threonine | 3.02 ± 0.27 µM |
| GST-Myt1 | Threonine/Tyrosine | 1.17 ± 0.22 µM |
| GST-CHK1 | Serine/Threonine | 1.42 ± 0.16 µM |
| GST-PLK1 | Serine/Threonine | 1.95 ± 0.07 µM |

SCYTONEMIN AND METHODS OF USING THEREOF

RELATED APPLICATION DATA

This application claims the benefit of U.S. Provisional Patent Application No. 60/185,029, filed Feb. 25, 2000, naming Robert S. Jacobs, Christopher S. Stevenson, William H. Gerwick, and Lisa A. Marshall as inventors, which is herein incorporated by reference.

STATEMENT REGARDING FEDERALLY SPONSORED RESEARCH OR DEVELOPMENT

This invention was made with Government support under Grant No. NA66RG0477, awarded by the National Oceanic & Atmospheric Administration (NOAA). The Government has certain rights in this invention.

BACKGROUND OF THE INVENTION

1. Field of the Invention

The present invention generally relates to compounds having a scytoneman skeleton, such as scytonemin. Specifically, the present invention relates to methods of using a compound having a scytoneman skeleton to inhibit, prevent, modulate, or attenuate cell-cycle progression, cell proliferation, kinase activity, phosphorylation, or induce apoptosis. Additionally, the present invention relates to methods of treating, preventing, or inhibiting diseases and disorders associated with cell cycle progression, cell proliferation, kinase activity, or angiogenesis in a subject comprising administering a scytoneman compound to the subject.

2. Description of the Related Art

The cell cycle is a tightly regulated series of events, eventually leading to the formation of two daughter cells. The transitions of the cell cycle are controlled by the reversible phosphorylation of certain proteins. For example, the cyclin-dependent kinases (CDKs) when complexed with a specific cyclin protein, are responsible for coordinating the passage of the cell through the different stages of the cell cycle. See Norbury, C. et al. (1992) Ann. Rev. Biochem. 61:441–470; Sherr, C. J. (1993) Cell 73:1059–1065; and Nasmyth, K. (1993) Curr. Opin. Cell Biol. 5:166–179. The phosphorylation of certain residues on CDK/cyclin complexes control catalytic activity both positively or negatively. See De Bondt, H. L. et al. (1993) Nature 363:595–602; Ducommun, B. et al. (1991) EMBO J 10:3311–3319; Jeffrey, P. D. et al. (1995) Nature 376:313–320. For instance, the catalytic activity of CDK1/cyclin B requires the removal of inhibitory phosphates by the cdc25C phosphatase. See Dunphy, W. G. et al. (1991) Cell 67:189–196. Subsequent activity of CDK1/cyclin B allows the cycle to progress from $G_2$ into mitosis. See Maller, J. L. (1991) Curr. Opin. Cell Biol. 3:269:275; Krek, W. et al. (1991) EMBO J 10:3321–3329; Atherton, F. S. et al. (1993) Mol. and Cell. Biol. 13:1675–1685; Endicott, J. A. et al. (1994) Prot. Eng. 7:243–253.

Aberrant cell proliferation is symptomatic of many debilitating disease conditions including rheumatoid arthritis, chronic obstructive pulmonary disorder, psoriasis, and cancers. Genetics research has advanced our knowledge as to what factors contribute to regulating the cell cycle. Many of these molecules have been targeted for pharmacological inactivation in attempts to discover novel mechanisms by which uncontrolled cell proliferation may be abrogated.

Recent evidence indicates that a novel family of enzymes, the polo-like kinases (Plks), may serve to regulate the activity of cdc25C. A Xenopus Plk (Plx1), and the human Plk homologue (PKL1), have both been implicated in the phosphorylation and subsequent activation of cdc25C. See Kumagai, A. et al. (1996) Science 273:1377–1380; Roshak, A. K. et al. (2000) Cellular Signaling 12:405–411. These findings suggest that the Plks constitute another level of regulation for CDKs, in particularly the activation of the CDK1/cyclin B complex via activation of cdc25C.

The polo gene was originally identified in *Drosophila melanogaster*, where mutant polo phenotypes displayed aberrant mitotic divisions due to abnormal spindle formation. See Sunkel and Glover, (1988) J. Cell Sci. 89:25–38. Functional homologues have subsequently been identified in organisms ranging from protozoa to human. See Graham, T. M. et al. (1998) Gene 207:71–77; Kitada, K. et al. (1993) Mol. Cell. Biol. 13:4445–4457; Ohkura et al. (1995) Genes & Dev. 9:1059–1073; Kumagai (1996); Clay et al. (1993) PNAS USA 90: 4882–4886; Golsteyn, et al. (1994) J. Cell Sci. 107:1509–1517; Hamanaka, et al. (1994) Cell Growth Differ. 5:249–257. Members of this family of serine/threonine kinases share homologous structural features which includes a 30 amino acid motif at the C-terminus, called the polo-box, the function of which is unknown. See Golsteyn, et al. (1996) Cell Cycle Res. 2:107–114; and Nigg (1998) Curr. Opin. Cell Biol. 10:776–783. Polo-family members also share a conserved sequence in the ATP binding domain. This conserved sequence, GxGGxAxC, differs from the sequences of ATP binding pockets of most other serine/threonine kinases, GxGxxGxV, wherein "x" is any nucleotide. See Golsteyn et al. (1996) and Nigg (1998).

Functional studies suggest that Plk homologues play an integral role in regulating cell cycle progression. See Lane, et al. (1996) J. Cell Biol. 135:1701–1713; Llamazares, et al. (1991) Genes Dev. 5:2153–2165; and Ohkura et al. (1995). The expression of PLK1 correlates with the mitotic index of many cancer cell lines. Over-expression of the enzyme in murine NIH3T3 cells results in a transformed phenotype. See Smith, et al. (1997) Biochem. Biophys. Res. Commun. 150:1165–1172. In addition, when PLK1-neutralizing antibodies are microinjected into a T cell line, the T cells lose the ability to undergo mitosis. See Lane (1996). These data suggest that PLK1 plays a critical role in cell cycle regulation and targeting its activity may yield another means of inhibiting aberrant cell proliferation.

Prior to the present invention, there have been no reports of small molecule inhibitors of PLK1 activity. Thus, there is a need for a polo-like kinase inhibitor for the treatment of cancer and other diseases and disorders associated with aberrant cell cycle progression and cell proliferation.

SUMMARY OF THE INVENTION

In some embodiments, the present invention relates to a method of inhibiting, modulating, attenuating, or preventing cell-cycle progression, intracellular signaling, or cell proliferation of a cell comprising exposing the cell to at least one scytoneman compound. In preferred embodiments, the scytoneman compound is scytonemin.

In some embodiments, the present invention relates to a method of inhibiting, modulating, attenuating, or preventing a kinase, kinase activity, or phosphorylation of a substrate by a kinase comprising exposing the kinase to at least one scytoneman compound. In preferred embodiments, the kinase is a cell cycle regulatory kinase or an intracellular signaling kinase. In some embodiments, the kinase is a serine/threonine kinase, a threonine/tyrosine kinase, or a tyrosine kinase, preferably, a polo-like kinase, a cyclin-dependent kinase, or a checkpoint kinase, more preferably, PLK1, Myt1, CHK1, CDK1/cyclinB, PKCβ2, PKA, or Tie2.

In some embodiments, the present invention relates to a method of treating, preventing, or inhibiting a disease or disorder associated with inflammation, cell cycle progression, cell proliferation, kinase activity, tissue hyperplasia or angiogenesis in a subject comprising administering at least one scytoneman compound to the subject. Preferably, the subject is a mammal, more preferably, human. In some embodiments, the disease or disorder is an acute or a chronic inflammatory disease or disorder. In some embodiments, the disease or disorder is cancer, a papilloma, rheumatoid arthritis, psoriasis, atherosclerosis, diabetic retinopathy, chronic obstructive pulmonary disorder, tuberculosis, chronic cholecystitis, osteoarthritis, rheumatic carditis, bronchiectasis, Hashimoto's thyroiditis, ulcerative colitis, Crohn's disease, silicosis, or the like. In preferred embodiments, the disease or disorder is cancer, rheumatoid arthritis, angiogenesis, or psoriasis. Preferably, the scytoneman compound is administered in a therapeutically effective amount or concentration.

In some embodiments, the present invention relates to a method of inducing apoptosis in a cell comprising exposing the cell to at least one scytoneman compound. In some embodiments, the present invention relates to a method of treating a disease, disorder, or tissue, in a subject comprising inducing apoptosis in a target by administering at least one scytoneman compound to the subject. In preferred embodiments, the target is a cell, an abnormal cell, or an organism.

In some embodiments, the present invention relates to a method of treating, preventing, inhibiting, attenuating or modulating inflammation related to an neurogenic inflammatory pathway in a subject comprising administering at least one scytoneman compound to the subject.

In some embodiments, the present invention relates to a method of treating, preventing, or inhibiting pain associated with neurogenic inflammation in a subject comprising administering at least one scytoneman compound to the subject.

It is to be understood that both the foregoing general description and the following detailed description are exemplary and explanatory and are intended to provide further explanation of the invention as claimed. The accompanying drawings are included to provide a further understanding of the invention and are incorporated in and constitute part of this specification, illustrate several embodiments of the invention and together with the description serve to explain the principles of the invention.

DESCRIPTION OF THE DRAWINGS

FIG. 7 shows the effect SCY has on other kinase activities.

DETAILED DESCRIPTION OF THE INVENTION

Figure 1:
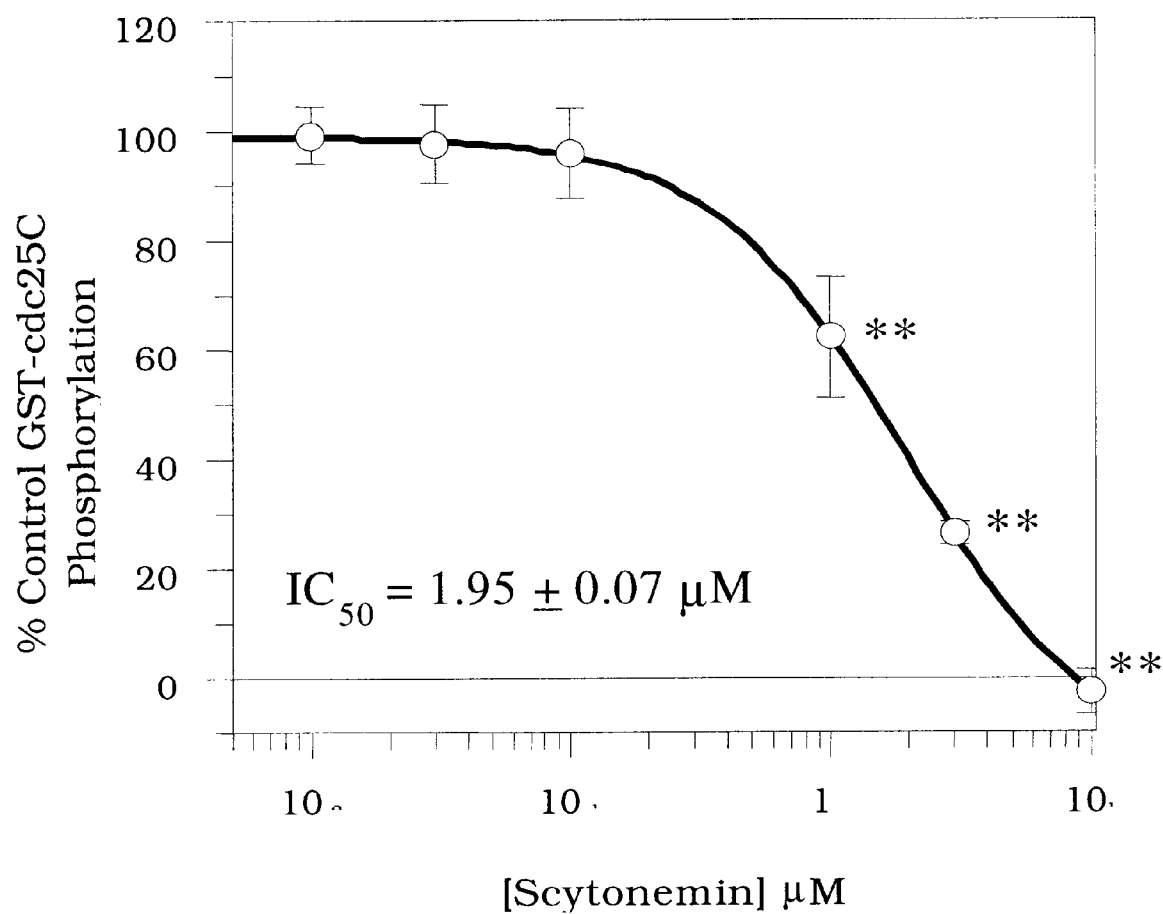
FIG. 1 illustrates that scytonemin inhibits GST-PLK1 phosphorylation of GST-cdc25C. All error bars represent standard deviation; *p<0.05; **p<0.01; $IC_{50}$ value given as $IC_{50}$±S.E.M.

The present invention is directed to kinase inhibitors and methods of using thereof to inhibit, prevent, modulate, or attenuate cell-cycle progression, cell proliferation, kinase activity, phosphorylation, or induce apoptosis.

The present invention is also directed to methods of using the kinase inhibitors to treat, prevent, or inhibit diseases and disorders associated with cell cycle progression, cell proliferation, kinase activity, tissue hyperplasia, angiogenesis, or a combination thereof such as cancer, papillomas, acute and chronic inflammation, rheumatoid arthritis, psoriasis, atherosclerosis, diabetic retinopathy, chronic obstructive pulmonary disorder, tuberculosis, chronic cholecystitis, osteoarthritis, rheumatic carditis, bronchiectasis, Hashimoto's thyroiditis, inflammatory bowel diseases such as ulcerative colitis and Crohn's disease, silicosis, and the like.

In some embodiments, the kinase inhibitor inhibits a serine/threonine, a threonine/tyrosine kinase, or a tyrosine kinase. In some embodiments, the kinase inhibitor inhibits an intracellular signaling kinase, a cell cycle regulatory kinase, or both. In preferred embodiments, the kinase inhibitor inhibits a polo-like, PKC, cyclin-dependent or checkpoint kinase, or the like. In most preferred embodiments, the kinase inhibitor inhibits PLK1, Myt1, CHK1, CDK1/cyclinB, PKCβ2, PKA, or Tie2.

Recently, it has been found that scytonemin (SCY), which has a unique structure comprised of indolic and phenolic subunits, generally known as the "scytoneman skeleton", exhibits antiproliferative activity and the ability to inhibit numerous protein kinases that play an integral role in mediating cellular signals involved in cell proliferation. SCY is a yellow-green pigment that was first isolated from sheathed cyanobacteria in the late 1870's. SCY is produced by organisms in response to ultraviolet (UV) radiation and is believed to be the earliest known UV screening strategy adapted by living organisms. The sheathed bacteria which produce SCY have been found in diverse geographic regions wherever exposure to strong solar irradiation occurs and includes freshwater, terrestrial, and marine habitats. Until now, only ultraviolet absorbing properties and anti-inflammatory activity when applied topically to skin have been documented for SCY. For example, see U.S. Pat. Nos. 5,461,070, 5,498,405, and 5,508,026, all of which are herein incorporated by reference.

As disclosed herein, SCY was found to be a mixed and time independent inhibitor of PLK1. It was also discovered to inhibit Myt1, CHK1, CDK1/cyclinB, and PKCβ2. At higher concentrations, SCY was found to inhibit PKA and GST-Tie2 (Tie2). Thus, SCY was less potent in inhibiting the activity of both PKA and Tie2 as compared with PLK1, Myt1, CDK1/cyclinB, and PKCβ2. All of these kinases are involved in various aspects of cell cycle progression and intracellular signaling. PLK1 is believed to be involved in mitotic spindle formation, centrosomal maturation, and the regulation of CDK1/cyclinB activity. Tie2 is a tyrosine kinase receptor integral in the regulation of angiogenesis, PKA and PKCβ2 are ubiquitous signaling kinases involved in a variety of regulatory pathways, and CDK1, Myt1, and CHK1 are involved regulating cell cycle events such as G2/M transition. Therefore, the present invention provides a method of inhibiting, modulating, attenuating, or preventing cell cycle progression, intracellular signaling, or both of a cell comprising exposing the cell to a scytoneman compound.

In some embodiments, the present invention is directed to a method of modulating cell growth by inhibiting a kinase of a cell comprising exposing the cell to a scytoneman compound. In preferred embodiments, the kinase is a cell cycle regulatory kinase or an intracellular signaling kinase such as a polo-like, PKC, cyclin-dependent or checkpoint kinase, or the like. More preferably, the kinase is PLK1, Myt1, CHK1, CDK1/cyclinB, PKCβ2, PKA, or Tie2. In a preferred embodiment, the present invention is directed to controlling aberrant or abnormal cell growth by inhibiting a kinase such as PLK1 with a scytoneman compound such as scytonemin.

Figure 3:
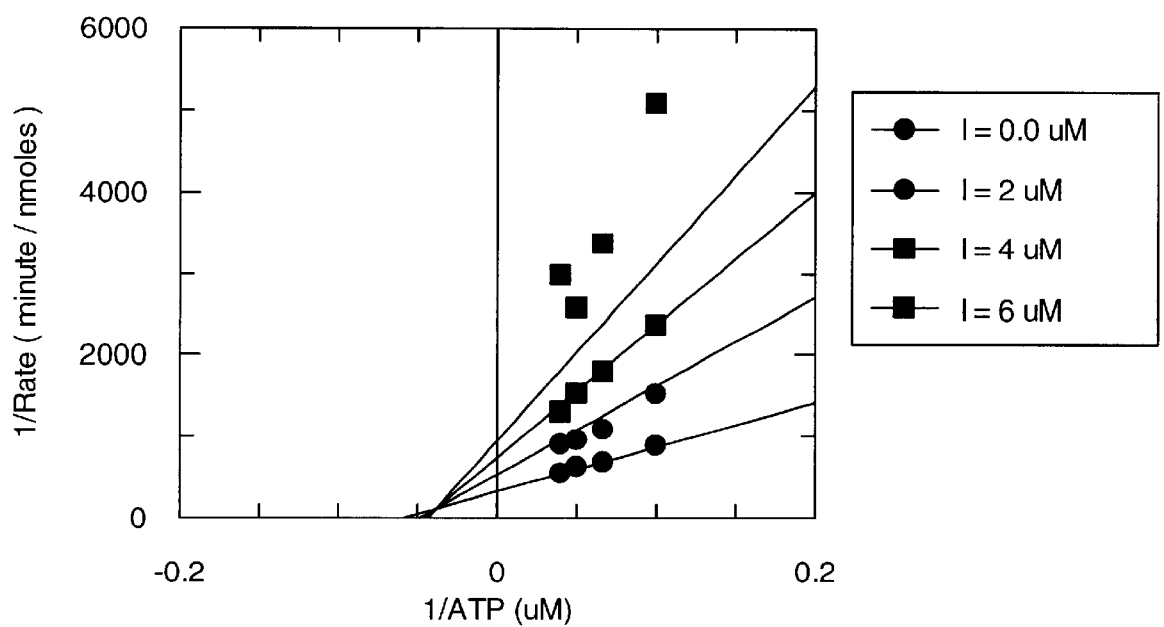
FIG. 3 illustrates that scytonemin is a mixed inhibitor of GST-PLK1 activity.
Figure 4:
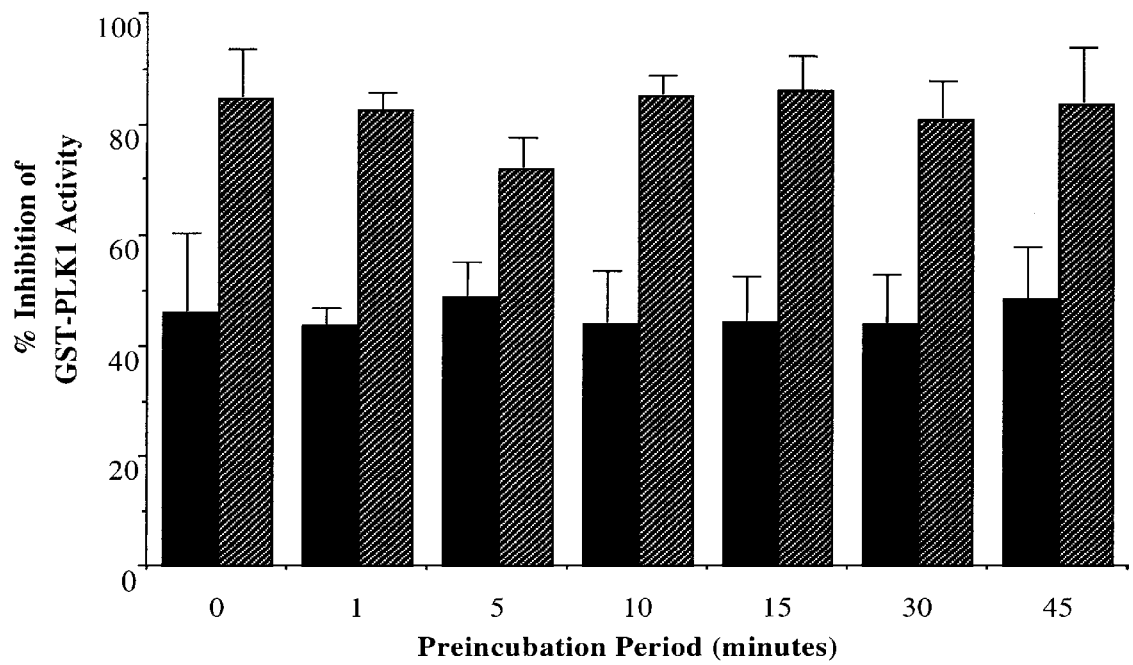
FIG. 4 illustrates the time course of scytonemin inhibition. Error bars represent standard deviation.

As disclosed herein and illustrated in Example 1, SCY inhibited the ability of GST-PLK1 to phosphorylate GST-cdc25C in a concentration-dependent manner with an $IC_{50}$ of 1.95±0.07 µM. See FIG. 1. FIG. 4 shows that there were no time dependent aspects to the inhibition, thereby indicating that SCY is a reversible inhibitor of GST-PLK1. As shown in Example 1, SCY is a mixed inhibitor of GST-PLK1 activity. FIG. 3 illustrates that the inhibition is primarily non-competitive in nature. Thus, SCY may be acting as an allosteric inhibitor of these kinases and at sufficiently high concentrations, the compound may be sterically interfering with the ability of ATP to attach to the binding pocket of the kinases.

To determine the specificity of the inhibition of SCY on GST-PLK1 activity, other kinase activity assay systems were used. The initial studies used kinases not directly involved in regulating CDK1 activation, but involved in processes related to the progression of hyperproliferative diseases. GST-Tie2 and PKA were affected or inhibited with high SCY concentrations. Specifically, the $IC_{50}$'s of SCY inhibition for Tie2 and PKA were greater than about 10 µM. Conversely, low SCY concentrations, less than about 10 µM, more preferably less than about 5 µM, were found to inhibit rhPKC, CDK1, GST-Myt1, and GST-CHK1. Therefore, SCY inhibits multiple kinases involved in intracellular signaling, cell cycle progression, and other cellular events with varying degrees of potency, which may be due to similarities of in the three-dimensional structure of the proteins at or surrounding the ATP binding site. See FIG. 7.

As SCY exhibits different degrees of potency for inhibiting, modulating, or attenuating various kinases and is generally non-competitive as shown by the ATP competition experiments disclosed herein, SCY may be binding the allosteric sites of these kinases, or sterically interfering with the ability of ATP to attach to the binding pocket of these kinases, thereby inhibiting the ability of these kinases to phosphorylate their substrates and negating the possibility that SCY is a chelating agent or an ATP or substrate analogue.

Thus, present invention provides a method of inhibiting, modulating, or attenuating the activity of a kinase in a cell comprising exposing the cell to a scytoneman compound. In some embodiments, the kinase is a serine/threonine, a threonine/tyrosine kinase, or a tyrosine kinase. In some embodiments, the kinase is an intracellular signaling kinase, a cell cycle regulatory kinase, or both. In preferred embodiments, the kinase is polo-like, PKC, cyclin-dependent or checkpoint kinase, or the like. In most preferred embodiments, the kinase is PLK1, Myt1, CHK1, CDK1/cyclinB, PKCβ2, PKA, or Tie2.

The present invention also provides a method of inhibiting, modulating, attenuating, or preventing the activity of multiple kinases with various degrees of potency comprising using a scytoneman compound. Further, the present invention provides a method of inhibiting, modulating, attenuating, or preventing the ability of a kinase to phosphorylate its corresponding substrate comprising exposing the kinase to a scytoneman compound. In some embodiments, the kinase is an intracellular signaling kinase or a cell cycle regulatory kinase. In preferred embodiments, the kinase is a polo-like, PKC, cyclin-dependent or checkpoint kinase, or the like. More preferably, the kinase is PLK1, Myt1, CHK1, CDK1/cyclinB, PKCβ2, PKA, or Tie2. In preferred embodiments, the substrate is cdc25C, CDK1, Myt1, Tie2, or the like.

The examples herein show that SCY blocks kinase activity which results in the inhibition of growth factor-induced cell proliferation. The examples also show that SCY may be used as an anti-proliferative agent and may be used to treat cancer and other diseases and disorders associated with proliferation. For example, rheumatoid synovial fibroblasts, isolated directly from patients diagnosed with rheumatoid arthritis (RA), were stimulated with PDGF-BB. This system was designed to simulate, in a controlled manner, some of the conditions present in the joints of RA patients. See Butler, et al. (1988) J. Rheumatol. 15:1463–1470, which is herein incorporated by reference. Both PDGF-BB and its receptor were found at abnormally high concentrations in RA patients compared to non-diseased joints. See Remmers, et al. (1991) J. Rheumatol. 18:7–13; and Rubin, et al. (1988) Scand. J. Immunol. 27:285–294, both of which are herein incorporated by reference. This is thought to contribute to the proliferation of the synoviocytes causing the swollen, deformed joints phenotypically characteristic of RA patients. The ECGF-induced HUVEC system was developed and is similar to one used to identify agents that may be effective in inhibiting angiogenesis, a process involved in all hyperproliferative disorders. See Folkman, et al. (1980) Nature 288:551–556, which is herein incorporated by reference. NHLFs and Jurkat T cells were two cell lines stimulated by serum to represent a "normal" and cancerous cell population, respectively. In all four cases, SCY effectively reduced the proliferation of these cells in response to a stimulus in a concentration-dependent manner with $IC_{50}$'s comparable to one another in the low micromolar range, about 1 µM to about 30 µM SCY. See FIGS. 5a–d.

Figure 9:
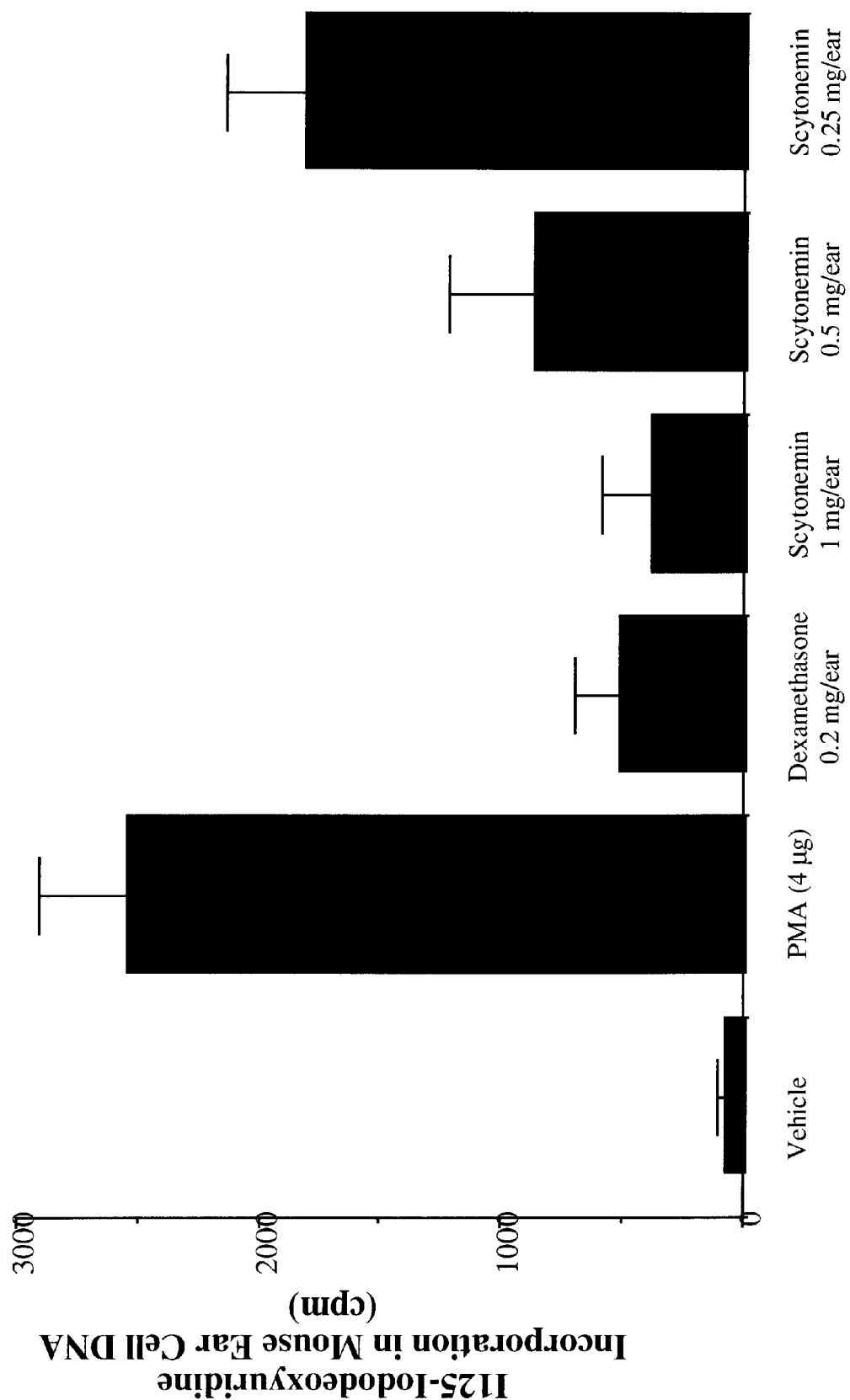
FIG. 9 shows that scytonemin prevents cell proliferation in vivo. Data presented as the average of the raw cpm values corrected for background (% control=–(1–((sample cpm–background))/(control cpm–background cpm)) (n=3). Statistical data was calculated using Excel. Error bars represent standard deviation; *=p<0.05 and **=p<0.01.

Additionally, as illustrated in Example 11 and FIG. 9, scytonemin effectively reduced or prevented cell proliferation in vivo. Thus, scytoneman compounds may be used to prevent, inhibit, modulate, or attenuate cell proliferation in vivo and in vitro. Further, as illustrated by these experiments, scytoneman compounds may be used to treat, prevent, or inhibit, diseases and disorders relating to cell proliferation such as rheumatoid arthritis, angiogenesis, cancer, and the like.

The present invention is directed to a method of treating, preventing, or inhibiting a disease or disorder associated with cell cycle progression, cell proliferation, kinase activity, tissue hyperplasia, or angiogenesis in a subject comprising administering a scytoneman compound to the subject. Preferably, the disease or disorder is cancer, papillomas, acute or chronic inflammation, rheumatoid arthritis, psoriasis, atherosclerosis, diabetic retinopathy, chronic obstructive pulmonary disorder, tuberculosis, chronic cholecystitis, osteoarthritis, rheumatic carditis, bronchiectasis, Hashimoto's thyroiditis, inflammatory bowel diseases such as ulcerative colitis and Crohn's disease, silicosis, or the like. Preferably, the subject is mammalian, more preferably, human. The kinase activity is preferably due to the activity of a cell cycle regulatory kinase or an intracellular signaling kinase such as a polo-like, PKC, cyclin-dependent or checkpoint kinase, or the like. In preferred embodiments, the kinase activity is due to PLK1, Myt1, CHK1, CDK1/cyclinB, PKCβ2, PKA, or Tie2.

In order to determine whether SCY was acting as a cytostatic or cytotoxic agent, the assay as disclosed in Example 8 was conducted to understand SCY's effects on the cell cycle and whether it induced the cells to undergo apoptosis. Flow cytometric analysis revealed that SCY displayed no ability to arrest the cells in any one phase of the cell cycle, but did cause the cells to undergo apoptosis. Thus, in a non-cell cycle dependent manner, SCY induced apoptosis in Jurkat T cells. Therefore, the present invention is directed to a method of inducing apoptosis in a cell comprising exposing the cell to a scytoneman compound. The present invention also includes methods of treating diseases, disorders, and tissues which may benefit from induced apoptosis such as cancers, rheumatoid arthritis, psoriasis, athersclerosis, and the like.

Resiniferatoxin (RTX) is an extremely irritant diterpene and a potent analog of capsaicin (CAP). The physiological effects of RTX and CAP are pain and neurogenic edema and they act by selectively stimulating nociceptive and thermal-sensitive nerve endings in tissues via interaction with a specific membrane receptor. The neurogenic edema is believed to be evoked by neuropeptides, substance P, calcitonin gene-regulated peptide, and others, released from primary afferent C-fiber nerve terminals and by histamine, secondarily released from nearby mast cells. The mode of action differs significantly from PMA-induced inflammation as PMA elicits its pro-inflammatory effects through cellular activation of specific immune cells such as macrophages and neutrophils.

As disclosed herein, scytoneman compounds prevent or inhibit inflammation caused by PMA and RTX, thereby indicating that scytoneman compounds may be used to treat, prevent, or inhibit inflammatory diseases and disorders relating to either an immunogenic (PMA) or a neurogenic (RTX) inflammatory pathway, or both. Additionally, as neurogenic inflammation is often associated with pain and scytonemin exhibits some analgesic properties, the scytoneman compounds may be used to treat, prevent, or inhibit pain resulting from inflammation. Therefore, the present invention provides a method of treating, preventing, inhibiting, attenuating or modulating a disease or disorder relating to neurogenic inflammation such as acute inflammation. The present invention also provides a method of preventing, inhibiting, attenuating or modulating a neurogenic inflammatory pathway. The present invention also provides methods of treating, preventing, inhibiting, attenuating or modulating tissue inflammation by reducing cytokine production, eicosanoid production, or both by administering a scytoneman compound of the present invention. As neurogenic inflammation is often associated with pain and scytonemin exhibits analgesic properties, the present invention is also directed to a method of treating, preventing or inhibiting pain associated with inflammation.

As used herein, the phrases "associated with" or "related to" refer to diseases and disorders that may be treated, prevented, or inhibited by inhibiting, modulating, attenuating, or preventing the activity of a given kinase. Also as used herein, "scytoneman compound" refers to a compound having the scytoneman skeleton, which is comprised of indolic and phenolic subunits, as illustrated by the following Structural Formula 1:

Structural Formula 1

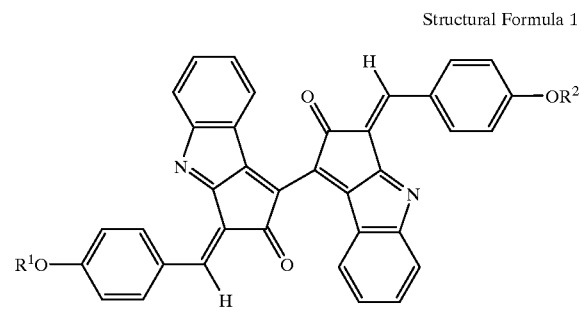

wherein $R^1$ and $R^2$ are independently H, an alkyl group having up o 5 carbon atoms, or $-CO-(CH_2)_n-CH_3$ where n=O to 16.

SCY has the following Structural Formula 2:

Structural Formula 2

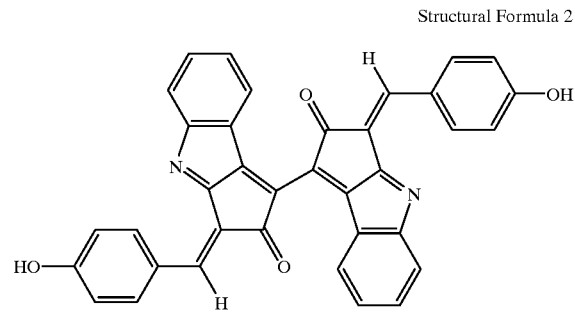

The terms and abbreviations used in the instant disclosure have their normal meanings unless otherwise designated.

As used in the present application, the following definitions apply:

In accordance with a convention used in the art,

is used in structural formulas herein to depict the bond that is the point of attachment of the moiety or substituent to the core or backbone structure.

Where chiral carbons are included in chemical structures, unless a particular orientation is depicted, both sterioisomeric forms are intended to be encompassed.

An "alkyl group" is intended to mean a straight or branched chain monovalent radical of saturated and/or unsaturated carbon atoms and hydrogen atoms, such as methyl (Me), ethyl (Et), propyl (Pr), isopropyl (i-Pr), butyl (Bu), isobutyl (i-Bu), t-butyl (t-Bu), ethenyl, pentenyl, butenyl, propenyl, ethynyl, butynyl, propynyl, pentynyl, hexynyl, and the like, which may be unsubstituted (i.e., contain only carbon and hydrogen) or substituted by one or more suitable sustituents as defined below (e.g., one or more halogen, such as F, Cl, Br, or I, with F and Cl being preferred). A "lower alkyl group" is intended to mean an alkyl group having from 1 to 8 carbon atoms in its chain.

A "cycloalkyl group" is intended to mean a non-aromatic monovalent monocyclic, bicyclic, or tricyclic radical comprising 3–14 carbon ring atoms, each of which may be saturated or unsaturated, and which may be unsubstituted or substituted by one or more suitable substituents as defined below, and to which may be fused one or more heterocycloalkyl groups, aryl groups, or heteroaryl groups, which themselves may be unsubstituted or substituted by one or more substituents. Illustrative examples of cycloalkyl groups include the following moieties:

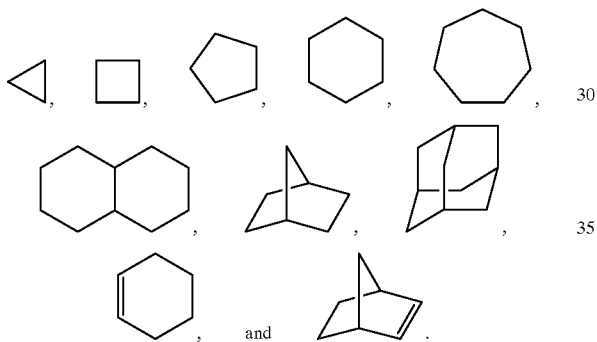

A "heterocycloalky group" is intended to mean a non-aromatic monovalent monocyclic, bicyclic, or tricyclic radical, which is saturated or unsaturated, comprising 3–18 ring members, which includes 1–5 heteroatoms selected from nitrogen, oxygen, and sulfur, where the radical is unsubstituted or substituted by one or more suitable substituents as defined below, and to which may be fused one or more cycloalkyl groups, aryl groups, or heteroaryl groups, which themselves may be unsubstituted or substituted by one or more suitable substituents. Illustrative examples of heterocycloalkyl groups include the following moieties:

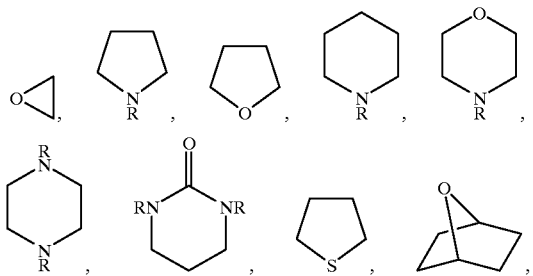

-continued

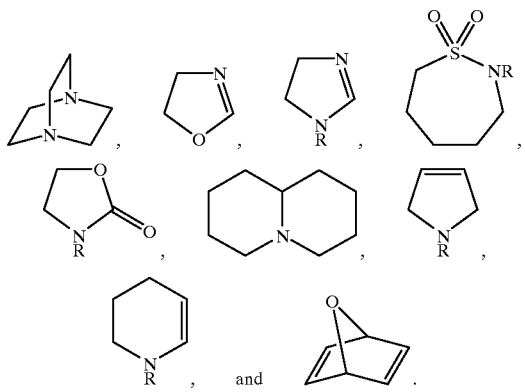

An "aryl group" is intended to mean an aromatic monovalent monocyclic, bicyclic, or tricyclic radical comprising 6, 10, 14, or 18 carbon ring members, which may be unsubstituted or substituted by one or more suitable substituents as defined below, and to which may be fused one or more cycloalkyl groups, heterocycloalkyl groups, or heteroaryl groups, which themselves may be unsubstituted or substituted by one or more suitable substituents. Thus, the term "aryl group" includes a benzyl group (Bzl). Illustrative examples of aryl groups include the following moieties:

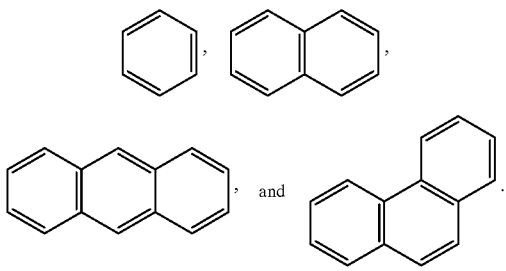

A "heteroaryl group" is intended to mean an aromatic monovalent monocyclic, bicyclic, or tricyclic radical comprising 4–18 ring members, including 1–5 heteroatoms selected from nitrogen, oxygen, and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents. Illustrative examples of heteroaryl groups include the following moieties:

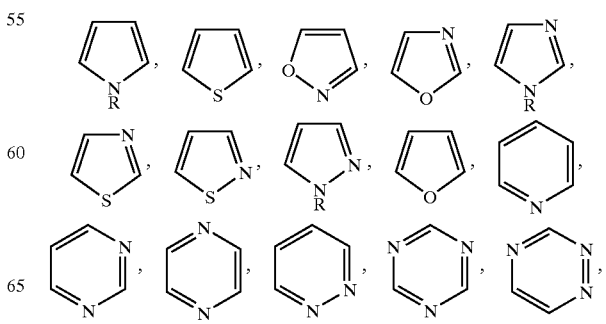

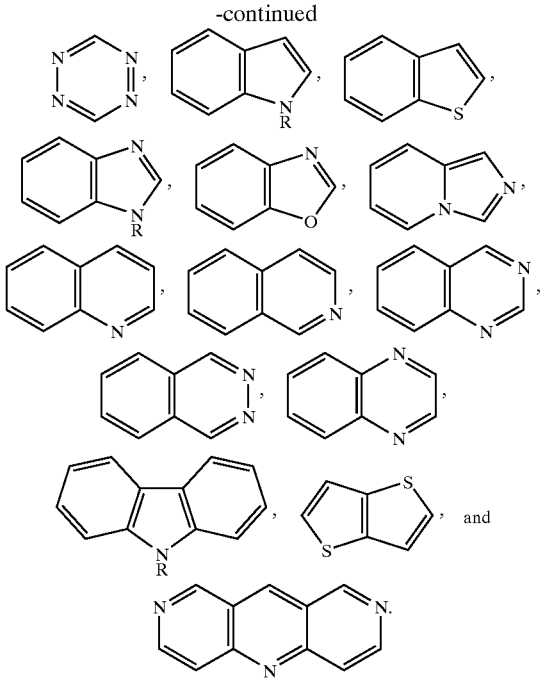

A "heterocycle" is intended to mean a heteroaryl or heterocycloalkyl group (each of which, as defined above, are optionally substituted).

The terms "aryl" (Ar) and "heteroaryl" refer to monocyclic and polycyclic unsaturated or aromatic ring structures, with "aryl" referring to those that are carbocycles and "heteroaryl" referring to those that are heterocycles. Examples of aromatic ring structures include phenyl, naphthyl, 1,2,3,4-tetrahydronaphthyl, furyl, thienyl, pyrrolyl, pyridyl, pyridinyl, pyrazolyl, imidazolyl, pyrazinyl, pyridazinyl, 1,2,3-triazinyl, 1,2,4-oxadiazolyl, 1,3,4-oxadiazolyl, 1-H-tetrazol-5-yl, indolyl, quinolinyl, benzofuranyl, benzothiophenyl (thianaphthenyl), and the like.

An "acyl group" is intended to mean a —C(O)—$R_a$ radical, where $R_a$ is a suitable substituent as defined below.

A "thioacyl group" is intended to mean a —C(S)—$R_a$ radical, where $R_a$ is a suitable substituent as defined below.

A "sulfonyl group" is intended to mean a —$SO_2R_a$ radical, where $R_a$ is a suitable substituent as defined below.

A "hydroxy group" is intended to mean the radical —OH.

An "amino group" is intended to mean the radical —$NH_2$.

An "alkylamino group" is intended to mean the radical —$NHR_a$, where $R_a$ is an alkyl group.

A "dialkylamino group" is intended to mean the radical —$NR_aR_b$, where $R_a$ and $R_b$ are each independently an alkyl group.

An "alkoxy group" is intended to mean the radical —$OR_a$, where $R_a$ is an alkyl group. Exemplary alkoxy groups include methoxy, ethoxy, propoxy, and the like.

An "alkoxycarbonyl group" is intended to mean the radical —$C(O)OR_a$, where $R_a$ is an alkyl group.

An "alkylsulfonyl group" is intended to mean the radical —$SO_2R_a$, where $R_a$ is an alkyl group.

An "alkylaminocarbonyl group" is intended to mean the radical —$C(O)NHR_a$, where $R_a$ is an alkyl group.

A "dialkylaminocarbonyl group" is intended to mean the radical —$C(O)NR_aR_b$, where $R_a$ and $R_b$ are each independently an alkyl group.

A "mercapto group" is intended to mean the radical —SH.

An "alkylthio group" is intended to mean the radical —$SR_a$, where $R_a$ is an alkyl group.

A "carboxy group" is intended to mean the radical —C(O)OH.

A "carbamoyl group" is intended to mean the radical —$C(O)NH_2$.

An "aryloxy group" is intended to mean the radical —$OR_c$, where $R_c$ is an aryl group.

A "heteroaryloxy group" is intended to mean the radical —$OR_d$, where $R_d$ is a heteroaryl group.

An "arylthio group" is intended to mean the radical —$SR_c$, where $R_c$ is an aryl group.

A "heteroarylthio group" is intended to mean the radical —$SR_d$, where $R_d$ is a heteroaryl group.

A "leaving group" (Lv) is intended to mean any suitable group that will be displaced by a substitution reaction. One of ordinary skill in the art will know that any conjugate base of a strong acid can act as a leaving group. Illustrative examples of suitable leaving groups include, but are not limited to, —F, —Cl, —Br, alkyl chlorides, alkyl bromides, alkyl iodides, alkyl sulfonates, alkyl benzenesulfonates, alkyl p-toluenesulfonates, alkyl methanesulfonates, triflate, and any groups having a bisulfate, methyl sulfate, or sulfonate ion.

A "protecting group" is intended to refer to groups that protect one or more inherent functional group from premature reaction. Suitable protecting groups may be routinely selected by those skilled in the art in light of the functionality and particular chemistry used to construct the compound. Examples of suitable protecting groups are described, for example, in Greene and Wutz, Protecting Groups in Organic Synthesis, $2^{nd}$ edition, John Wiley and Sons, New York, N.Y. (1991).

The term "suitable organic moiety" is intended to mean any organic moiety recognizable, such as by routine testing, to those skilled in the art as not adversely affecting the inhibitory activity of the inventive compounds. Illustrative examples of suitable organic moieties include, but are not limited to, hydroxyl groups, alkyl groups, oxo groups, cycloalkyl groups, heterocycloalkyl groups, aryl groups, heteroaryl groups, acyl groups, sulfonyl groups, mercapto groups, alkylthio groups, alkoxy groups, carboxy groups, amino groups, alkylamino groups, dialkylamino groups, carbamoyl groups, arylthio groups, heteroarylthio groups, and the like.

In general, the various moieties or functional groups for variables in the formulae may be "optionally substituted" by one or more suitable "substituents". The term "substituent" or "suitable substituent" is intended to mean any suitable substituent that may be recognized or selected, such as through routine testing, by those skilled in the art. Illustrative examples of useful substituents are those found in the exemplary compounds that follow, as well as halogen (chloro, iodo, bromo, or fluoro); $C_{1-6}$-alkyl; $C_{1-6}$-alkenyl; $C_{1-6}$-alkynyl; hydroxyl; $C_{1-6}$ alkoxyl; amino; nitro; thiol; thioether; imine; cyano; amido; phosphonato; phosphine; carboxyl; carbonyl; aminocarbonyl; thiocarbonyl; sulfonyl; sulfonamine; sulfonamide; ketone; aldehyde; ester; oxygen (═O); haloalkyl (e.g., trifluoromethyl); carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); nitro; thiol; thioether, O-lower alkyl; O-aryl, aryl; aryl-lower alkyl; $CO_2CH_3$; $CONH_2$; $OCH_2CONH_2$; $NH_2$; $SO_2NH_2$; $OCHF_2$; $CF_3$; $OCF_3$; and the like. Such moieties may also be optionally substituted by a fused-ring structure or bridge, for example $OCH_2$—O. All of these substituents may optionally be further substituted with a substituent selected from groups such as hydroxy groups, halogens, oxo groups, alkyl groups, acyl groups, sulfonyl groups, mercapto groups, alkylthio groups, alkyloxy groups, cycloalkyl groups, heterocycloalkyl groups, aryl groups, heteroaryl groups, carboxy groups, amino groups, alkylamino groups, dialkylamino groups, carbamoyl groups, aryloxy groups, heteroaryloxy groups, arylthio groups, heteroarylthio groups, and the like.

The term "optionally substituted" is intended to expressly indicate that the specified group is unsubstituted or substituted by one or more suitable substituents, unless the optional substituents are expressly specified, in which case the term indicates that the group is unsubstituted or substituted with the specified substituents. As defined above, various groups may be unsubstituted or substituted (i.e., they are optionally substituted) unless indicated otherwise herein (e.g., by indicating that the specified group is unsubstituted).

It is understood that while a scytoneman compound of the general structural formulas herein may exhibit the phenomenon of tautomerism, the structural formulas within this specification expressly depict only one of the possible tautomeric forms. It is therefore to be understood that the structural formulas herein are intended to represent any tautomeric form of the depicted compound and is not to be limited merely to a specific compound form depicted by the structural formulas.

It is also understood that the structural formulas are intended to represent any configurational form of the depicted compound and is not to be limited merely to a specific compound form depicted by the structural formulas.

Some of the scytoneman compounds may exist as single stereoisomers (i.e., essentially free of other stereoisomers), racemates, or mixtures of enantiomers, diastereomers, or both. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, if the compounds of the present invention are made synthetically, they are used in a form that is at least 90% optically pure, that is, a form that comprises at least 90% of a single isomer (80% enantiomeric excess (e.e.) or diastereomeric excess (d.e.), more preferably at least 95% (90% e.e. or d.e.), even more preferably at least 97.5% (95% e.e. or d.e.), and most preferably at least 99% (98% e.e. or d.e.).

Additionally, the structural formulas herein are intended to cover, where applicable, solvated as well as unsolvated forms of the compounds. A "solvate" is intended to mean a pharmaceutically acceptable solvate form of a specified compound that retains the biological effectiveness of such compound. Examples of solvates include compounds of the invention in combination with water, isopropanol, ethanol, methanol, dimethyl sulfoxide, ethyl acetate, acetic acid, ethanolamine, or acetone. Also included are miscible formulations of solvate mixtures such as a compound of the invention in combination with an acetone and ethanol mixture. In a preferred embodiment, the solvate includes a compound of the invention in combination with about 20% ethanol and about 80% acetone. Thus, the structural formulas include compounds having the indicated structure, including the hydrated as well as the non-hydrated forms.

As indicated above, the compounds of the invention also include active tautomeric and stereoisomeric forms of the scytoneman compounds of the Structural Formula 1 or 2, which may be readily obtained using techniques known in the art. For example, optically active (R) and (S) isomers may be prepared via a stereospecific synthesis, e.g., using chiral synthons and chiral reagents, or racemic mixtures may be resolved using conventional techniques.

Additionally, the compounds of the invention include pharmaceutically acceptable salts, multimeric forms, prodrugs, active metabolites, precursors and salts of such metabolites of the scytoneman compounds of the Structural Formula 1 or 2.

The term "pharmaceutically acceptable salts" refers to salt forms that are pharmacologically acceptable and substantially non-toxic to the subject being treated with the compound of the invention. Pharmaceutically acceptable salts include conventional acid-addition salts or base-addition salts formed from suitable non-toxic organic or inorganic acids or inorganic bases. Exemplary acid-addition salts include those derived from inorganic acids such as hydrochloric acid, hydrobromic acid, hydroiodic acid, sulfuric acid, sulfamic acid, phosphoric acid, and nitric acid, and those derived from organic acids such as p-toluenesulfonic acid, methanesulfonic acid, ethane-disulfonic acid, isethionic acid, oxalic acid, p-bromophenylsulfonic acid, carbonic acid, succinic acid, citric acid, benzoic acid, 2-acetoxybenzoic acid, acetic acid, phenylacetic acid, propionic acid, glycolic acid, stearic acid, lactic acid, malic acid, tartaric acid, ascorbic acid, maleic acid, hydroxymaleic acid, glutamic acid, salicylic acid, sulfanilic acid, and fumaric acid. Exemplary base-addition salts include those derived from ammonium hydroxides (e.g., a quaternary ammonium hydroxide such as tetramethylammonium hydroxide), those derived from inorganic bases such as alkali or alkaline earth-metal (e.g., sodium, potassium, lithium, calcium, or magnesium) hydroxides, and those derived from organic bases such as amines, benzylamines, piperidines, and pyrrolidines.

The term "multimer" refers to multivalent or multimeric forms of active forms of the compounds of the invention. Such "multimers" may be made by linking or placing multiple copies of an active compound in close proximity to each other, e.g., using a scaffolding provided by a carrier moiety. Multimers of various dimensions (i.e., bearing varying numbers of copies of an active compound) may be tested to arrive at a multimer of optimum size with respect to receptor binding. Provision of such multivalent forms of active receptor-binding compounds with optimal spacing between the receptor-binding moieties may enhance receptor binding (See, for example, Lee et al., (1984) Biochem. 23:4255). The artisan may control the multivalency and spacing by selection of a suitable carrier moiety or linker units. Useful moieties include molecular supports comprising a multiplicity of functional groups that can be reacted with functional groups associated with the active compounds of the invention. A variety of carrier moieties may be used to build highly active multimers, including proteins such as BSA (bovine serum albumin) or HSA, peptides such as pentapeptides, decapeptides, pentadecapeptides, and the like, as well as non-biological compounds selected for their beneficial effects on absorbability, transport, and persistence within the target organism. Functional groups on the carrier moiety, such as amino, sulfhydryl, hydroxyl, and alkylamino groups, may be selected to obtain stable linkages to the compounds of the invention, optimal spacing between the immobilized compounds, and optimal biological properties.

"A pharmaceutically acceptable prodrug" is a compound that may be converted under physiological conditions or by solvolysis to the specified compound or to a pharmaceutically acceptable salt of such compound. "A pharmaceutically active metabolite" is intended to mean a pharmacologically active product produced through metabolism in the body of a specified compound or salt thereof. Prodrugs and active metabolites of a compound may be identified using routine techniques known in the art. See, e.g., Bertolini, G. et al., (1997) J. Med. Chem. 40:2011–2016; Shan, D. et al., *J. Pharm. Sci.,* 86(7):765–767; Bagshawe K., (1995) Drug Dev. Res. 34:220–230; Bodor, N., (1984) Advances in Drug Res. 13:224–331; Bundgaard, H., *Design of Prodrugs* (Elsevier Press, 1985); and Larsen, I. K., *Design and Application of Prodrugs,* Drug Design and Development (Krogsgaard-Larsen et al., eds., Harwood Academic Publishers, 1991).

If the scytoneman compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyrvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the scytoneman compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds, agents and salts may exist in different crystal or polymorphic forms, all of which are intended to be within the scope of the present invention and specified structural formulas.

The activity, including inhibitory kinase activity and ability to induce apoptosis, of the scytoneman compounds may be measured by any of the methods available to those skilled in the art, including in vitro and in vivo assays. Examples of suitable assays for activity measurements are provided herein. Properties of the scytoneman compounds may be assessed, for example, by using one or more of the assays set out in the Examples below.

To test the activity of the compounds of the present invention in vivo, well-known pharmacological methods are used to determine the efficacy of the compounds as kinase inhibitors, anti-inflammatory agents, anti-proliferative agents, anti-neoplastic agents and apoptosis agents.

The scytoneman compounds in accordance with the present invention are useful in the treatment of diseases and disorders associated with cell cycle progression, cell proliferation, kinase activity, tissue hyperplasia, angiogenesis, or inflammation such as cancer, papillomas, acute and chronic inflammation, rheumatoid arthritis, psoriasis, atherosclerosis, diabetic retinopathy, chronic obstructive pulmonary disorder, tuberculosis, chronic cholecystitis, osteoarthritis, rheumatic carditis, bronchiectasis, Hashimoto's thyroiditis, inflammatory bowel diseases such as ulcerative colitis and Crohn's disease, silicosis, and the like.

The scytoneman compounds of the present invention may be used in combination with or as a substitution for treatments of the above conditions. For example, the scytoneman compounds may also be used alone or combination with an anti-neoplastic agent to treat cancer. The scytoneman compounds of the invention may be used alone or in combination with glucocorticoids, cyclooxygenase (COX) inhibitors, aspirin, or methotrexate to treat inflammatory disorders such as rheumatoid arthritis. Further, the scytoneman compounds of the present invention may be used alone or in combination with analgesics to treat, prevent or inhibit pain.

A scytoneman compound of the present invention may be administered in a therapeutically effective amount to a mammal such as a human. A therapeutically effective amount may be readily determined by standard methods known in the art. As defined herein, a therapeutically effective amount of a compound of the invention ranges from about 1 to about 2400 mg/kg body weight, preferably about 10 to about 1000 mg/kg body weight, and more preferably about 10 to about 500 mg/kg body weight. Preferred topical concentrations include about 0.1% to about 10% in a formulated salve. The skilled artisan will appreciate that certain factors may influence the dosage required to effectively treat a subject, including but not limited to the severity of the disease or disorder, previous treatments, the general health and/or age of the subject, and other diseases present.

Moreover, treatment of a subject with a therapeutically effective amount of the scytoneman compound can include a single treatment or, preferably, can include a series of treatments.

In a preferred example, a subject is treated with a compound of the invention in the range of between about 1 to about 2400 mg/kg body weight, at least one time per week for between about 1 to about 24 weeks, and preferably between about 1 to about 10 weeks. It will also be appreciated that the effective dosage of the compound used for treatment may increase or decrease over the course of a particular treatment. Changes in dosage may result and become apparent by standard diagnostic assays known in the art. In some conditions chronic administration may be required.

The pharmaceutical compositions of the invention may be prepared in a unit-dosage form appropriate for the desired mode of administration. The compositions of the present invention may be administered for therapy by any suitable route including oral, rectal, nasal, topical (including buccal and sublingual), vaginal and parenteral (including subcutaneous, intramuscular, intravenous and intradermal). It will be appreciated that the preferred route will vary with the condition and age of the recipient, the nature of the condition to be treated, and the chosen active compound.

It will be appreciated that the actual dosages of the agents used in the compositions of this invention will vary according to the particular complex being used, the particular composition formulated, the mode of administration, and the particular site, host, and disease being treated. Optimal dosages for a given set of conditions may be ascertained by those skilled in the art using conventional dosage-determination tests in view of the experimental data for a given scytoneman compound. Administration of prodrugs may be dosed at weight levels that are chemically equivalent to the weight levels of the fully active forms.

The scytoneman compounds of the invention can be incorporated into pharmaceutical compositions suitable for administration. Pharmaceutical compositions of this invention comprise a therapeutically effective amount of a scytoneman compound having the Structural Formula 1 or 2, and an inert, pharmaceutically acceptable carrier or diluent. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like. The use of such media and agents for pharmaceutically active substances is well known in the art.

Except insofar as any conventional media or agent is incompatible with the active compound, use thereof in the compositions is contemplated. Supplementary active compounds can also be incorporated into the compositions. Supplementary active compounds include glucocorticoids, cyclooxygenase (COX) inhibitors, aspirin, methotrexate, taxol, and the like.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of an inventive agent is dissolved in an aqueous solution of an organic or inorganic acid, such as 0.3 M solution of succinic acid or citric acid. If a soluble salt form is not available, the agent may be dissolved in a suitable cosolvent or combinations of cosolvents. Examples of suitable cosolvents include, but are not limited to, alcohol, propylene glycol, polyethylene glycol 300, polysorbate 80, glycerin and the like in concentrations ranging from 0–60% of the total volume. In an exemplary embodiment, the scytoneman compound of the present invention is dissolved in DMSO and diluted with water.

The composition may also be in the form of a solution of a salt form of the active ingredient in an appropriate aqueous vehicle such as water or isotonic saline or dextrose solution.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations which can be used pharmaceutically.

Proper formulation is dependent upon the route of administration chosen. For injection, the agents of the invention may be formulated into aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally comprise gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations which can be used orally include push-fit capsules made of gelatin, as well as soft, sealed capsules made of gelatin and a plasticizer, such as glycerol or sorbitol. The push-fit capsules can comprise the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can comprise any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Preferred formulations for oral formulations include microcrystalline tablets, gelatin capsules, or the like.

For administration intranasally or by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated comprising a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may comprise formulatory agents such as suspending, stabilizing and/or dispersing agents.

Pharmaceutical compositions suitable for injectable use include sterile aqueous solutions (where water soluble) or dispersions and sterile powders for the extemporaneous preparation of sterile injectable solutions or dispersion. Aqueous injection suspensions may comprise substances which increase the viscosity of the suspension, such as sodium carboxymethyl cellulose, sorbitol, or dextran. Optionally, the suspension may also comprise suitable stabilizers or agents which increase the solubility of the compounds to allow for the preparation of highly concentrated solutions. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes.

For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium comprising, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating a therapeutically effective amount of a compound of the invention in an appropriate solvent with one or a combination of ingredients enumerated above, as required, followed by filtered sterilization. Generally, dispersions are prepared by incorporating the scytoneman compound into a sterile vehicle which comprises a basic dispersion medium and the required other ingredients from those enumerated above. In the case of sterile powders for the preparation of sterile injectable solutions, the preferred methods of preparation are vacuum drying and freeze-drying which yields a powder of the active compound plus any additional desired ingredient from a previously sterile-filtered solution thereof.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, foams, powders, sprays, aerosols or creams as generally known in the art.

For example, for topical formulations, pharmaceutically acceptable excipients may comprise solvents, emollients, humectants, preservatives, emulsifiers, and pH agents. Suitable solvents include ethanol, acetone, glycols, polyurethanes, and others known in the art. Suitable emollients include petrolatum, mineral oil, propylene glycol dicaprylate, lower fatty acid esters, lower alkyl ethers of propylene glycol, cetyl alcohol, cetostearyl alcohol, stearyl alcohol, stearic acid, wax, and others known in the art. Suitable humectants include glycerin, sorbitol, and others known in the art. Suitable emulsifiers include glyceryl monostearate, glyceryl monoleate, stearic acid, polyoxyethylene cetyl ether, polyoxyethylene cetostearyl ether, polyoxyethylene stearyl ether, polyethylene glycol stearate, propylene glycol stearate, and others known in the art. Suitable pH agents include hydrochloric acid, phosphoric acid, diethanolamine, triethanolamine, sodium hydroxide, monobasic sodium phosphate, dibasic sodium phosphate, and others known in the art. Suitable preservatives include benzyl alcohol, sodium benzoate, parabens, and others known in the art.

For administration to the eye, the compound of the invention is delivered in a pharmaceutically acceptable ophthalmic vehicle such that the compound is maintained in contact with the ocular surface for a sufficient time period to allow the compound to penetrate the corneal and internal regions of the eye, including, for example, the anterior chamber, posterior chamber, vitreous body, aqueous humor, vitreous humor, cornea, iris/cilary, lens, choroid/retina and selera. The pharmaceutically acceptable ophthalmic vehicle may be an ointment, vegetable oil, or an encapsulating material. A compound of the invention may also be injected directly into the vitreous and aqueous humor.

Alternatively, the active ingredient may be in powder form for constitution with a suitable vehicle, e.g., sterile pyrogen-free water, before use. The compounds may also be formulated in rectal compositions such as suppositories or retention enemas, e.g., comprising conventional suppository bases such as cocoa butter or other glycerides.

In addition to the formulations described above, the compounds may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

A pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD cosolvent system (VPD:5 W) comprises VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied, for example: other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers comprising the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Some of the compounds of the invention may be provided as salts with pharmaceutically compatible counter ions. Pharmaceutically compatible salts may be formed with many acids, including hydrochloric, sulfuric, acetic, lactic, tartaric, malic, succinic, etc. Salts tend to be more soluble in aqueous or other protonic solvents than are the corresponding free-base forms.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit comprising a predetermined quantity of active compound calculated to produce the desired therapeutic effect in association with the required pharmaceutical carrier.

The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

Specifically, toxicity may be determined by the trypan blue exclusion test or the lactose dehydrogenase toxicity assay developed by Promega (Madison, Wis.).

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The scytoneman compounds of the present invention may be prepared using reaction routes, synthesis schemes and techniques available in the art using starting materials that are readily available.

The following examples are intended to illustrate but not to limit the invention.

EXAMPLE 1

GST-Plk Kinase Activity Kinetic Assays

GST-PLK1 and GST-cdc25C were synthesized as described in Roshak et al. (2000), which is herein incorporated by reference. GST-PLK1 and GST-cdc25C were purified to 20% and 60% purity as determined by SDS-PAGE analysis and Coomassie Blue staining. The remaining impurities were determined to be free GST.

Kinase reactions comprised 350 nM GST-cdc25C, 0.5 µCi [$^{33}$P]-γATP (NEN, Cambridge, Mass.), 10 µM unlabelled ATP (Sigma, St. Louis, Mo.), 20 nM GST-PLK1 in kinase reaction buffer comprising 20 mM HEPES (pH 7.4), 50 mM KCl, 10 mM MgCl$_2$, 1 mM EGTA, 0.5 mM DTT. Enzyme and substrates were diluted individually in kinase buffer and the PLK1 solution was pre-activated by incubating at 37° C. for 1 hour prior to its addition to the assay as described in Roshak et al. (2000).

50 µl reactions were conducted in 96 well polypropylene plates. First, 1 nM to 10 µM SCY dissolved in 100% DMSO was added, followed by the addition of enzyme and substrate to give a final concentration of 4% DMSO. The reactions were initiated by the addition of ATP. The reactions progressed for 60 minutes at 37° C., and were then stopped with 25 mM EDTA and 1 mM unlabeled ATP. The samples were transferred to 96 well 0.45 µm millipore filtration plates (Millipore, Bedford, Mass.), the proteins were precipitated with a 10% TCA, 5% sodium pyrophosphate solution (TCA-NaPP), and the plates were filtered using a Millipore microplate filtration unit (Millipore, Bedford, Mass.). The plates were washed twice with the TCA-NaPP solution, twice with 75 mM phosphoric acid, and twice with PBS. After drying at room temperature, scintillation fluid was added to the plate, and [$^{33}$P]-γATP incorporation was measured on a Packard Top-Count.

Analysis by autoradiography was performed as described in Roshak et al. (2000). Briefly, GST-PLK1 (20 nM/assay), 10 mM ATP, 1 µCi [$^{32}$P]-γATP, and 350 nM GST-cdc25C were incubated in microcentrifuge tubes (50 µl/assay) for 60 minutes at 37° C. in the presence of 1 to 10 µM SCY and 10 µM hymenialdisine. The reactions were terminated with 25 mM EDTA, separated by SDS-PAGE and GST-cdc25C phosphorylation was visualized using Imagequest (Molecular Dynamics, Sunnyvale, Calif.). 10 µM hymenialdisine served as a positive control for each assay described above.

Figure 2:
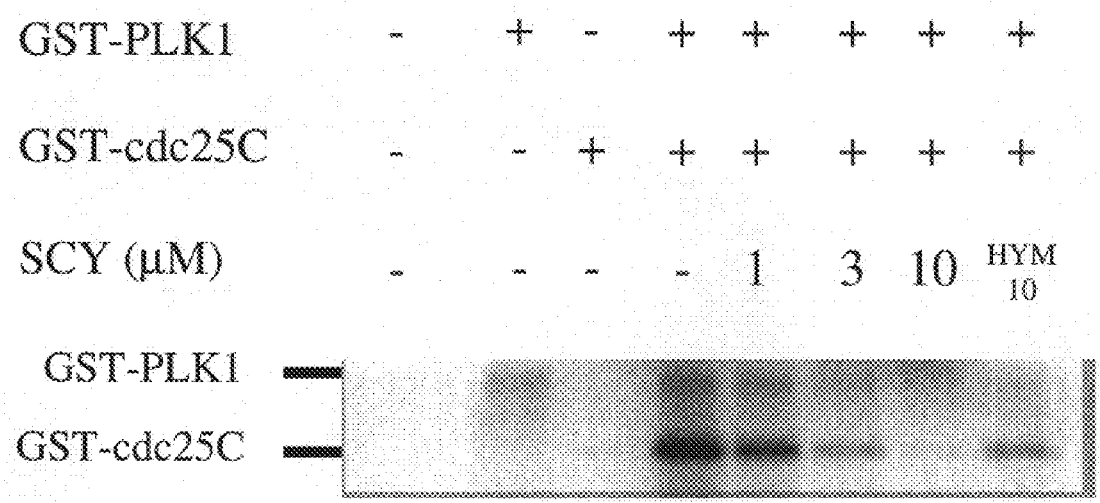
FIG. 2 is a phosphorimage of GST-PLK1 phosphorylation of GST-cdc25C in the presence of scytonemin.

As has been previously reported, GST-PLK1 readily phosphorylates GST-cdc25C. As shown in FIG. 1, when the reactions were run in the presence of increasing concentrations of SCY, the ability of GST-PLK1 to phosphorylate GST-cdc25C was inhibited in a concentration-dependent manner. Using this assay system, the IC$_{50}$ of SCY was determined to be 1.95±0.07 µM which was calculated using the Grafit statistical analysis program. As shown in FIG. 2, SCY markedly reduced the level of GST-cdc25C phosphorylation in a concentration-dependent manner with virtually no phosphorylated GST-cdc25C detectable in the presence of 10 µM SCY.

To determine whether SCY was acting as and ATP analogue, ATP competition assays were conducted as described above in the presence of increasing concentrations, 10, 15, 20, and 25 µM, of unlabeled ATP and three concentrations of SCY, 2, 4, and 6 µM SCY. The results were plotted using the Grafit statistical analysis program. The double-reciprocal shown in FIG. 3 indicate the mechanism for SCY may be one of a mixed inhibitor. Ki values generated by the Grafit program showed SCY to have neither the characteristics of a pure competitive nor pure noncompetitive inhibitor. See FIG. 3. The Ki value for SCY when fitting the data as a competitive inhibitor was 3.0±1.9 µM and when fitted as an uncompetitive inhibitor the Ki value was determined to be 2.3±1.9 µM.

To ascertain if inhibition of GST-PLK1 activity by SCY is time dependent, 3 µM and 10 µM SCY were pre-incubated with both enzyme and substrate for 0, 15, 30, and 45 minutes at room temperature. At the end of the pre-incubation period, ATP was added to initiate the activity assay. As shown in FIG. 4, there was no change in the level of inhibition by SCY at either concentration over any time period. GST-PLK1 activity was reduced by about 58% and about 93% after preincubation with 3 µM and 10 µM SCY, respectively, which is consistent with the levels shown in FIG. 3. Therefore, inhibition of GST-PLK1 activity by SCY is not time dependent.

EXAMPLE 2

GST-Myt1 Autophosphorvlation-DELFIA Assay

To determine the effect of SCY on GST-Myt1 activity, a rh-GST-Myt1 expression vector was constructed to include gst fused to the amino terminus of a truncated human Myt1 gene via a linker comprising a thrombin cleavage site. The Myt1 gene was truncated after amino acid 379 and just prior to the membrane-anchoring domain. The construct was cloned into the baculovirus expression system, pFASTBAC (Gibco-BRL, Gaithersburg, Md.).

Spodoptera frugiperda 9 (Sf9) cells were infected with the virus and grown for three days before purifying as described in Roshak et al. (2000) for GST-PLK1 and GST-cdc25C to 75% purity as determined by SDS-PAGE analysis and Coomassie Blue staining. Dissociative enhanced lanthanide fluorescence immunoassays (DELFIA) (Wallac OY, Turku, Finland) were performed in 50 µl/well with 0.25 µg GST-Myt1, in reaction buffer (50 mM HEPES, pH 7.4, 2 mM Mn(OAc)$_2$, 1 µM ATP, 1 mM DTT (final reaction concentrations)), and SCY (1 nM to 10 µM final reaction concentration). The positive control used was 10 µM hymenialdisine (final concentration) in a final vehicle concentration of 1% DMSO.

Reactions were allowed to proceed at room temperature with shaking for 20 minutes and were stopped with the addition of EDTA to give a final concentration of 20 mM, and the protein was allowed to bind to the wells for an additional 40 minutes. The wells were washed three times with 300 µl TBS/0.2% Tween. After washing, the plate was blocked using Pierce's Superblock) (Wallac OY, Turku, Finland) in TBS and then washed three times with 300 µl TBS/Tween. 100 µl of 0.125 µg/ml Eu-labeled anti-phosphotyrosine antibody in TBS/Tween comprising 0.15 mg/ml BSA was added to each well and incubated for 30 minutes with shaking at room temperature. The wells were washed three times with TBS/Tween. 200 µl of enhancement solution (Wallac OY, Turku, Finland) was added to each well and incubated with shaking for 10 minutes. The plate was then read on the 1420 VICTOR plate counter from Wallac, Inc.

GST-Myt1 was inhibited in a concentration-dependent manner by SCY. As illustrated in FIG. 7, the $IC_{50}$ for SCY was about 1 µM.

EXAMPLE 3

CDK1/CyclinB-Histone H1 Phosphorylation Assay

To determine the effect of SCY on CDK1/cyclinB1 kinase activity, the following assay was conducted. Baculovirus vectors expressing CDK1 and cyclinB 1, obtained from Dr. David Morgan of the University of California San Francisco, were expressed and purified by the method described in Desai, et al. (1992) Mol. Cell Biol. 3:571–582, which is herein incorporated by reference, to 80% purity as determined by SDS-PAGE analysis and Coomassie Blue staining. CDK1/cyclinB 1 kinase activity was analyzed in a 96-well flashplate assay using 2.0 µg/well bovine histone H1 as a substrate. Reactions were run in 50 µl with 0.25 µg of CDK1/cyclinB 1 complex, in reaction buffer (50 mM HEPES, pH 7.4, 10 mM $MgCl_2$, 0.1 µM ATP, 1 mM DTT and 0.5 µCi of $[\gamma^{33}\text{-P}]$ ATP (final reaction concentrations)), and SCY (1 nM to 10 µM final reaction concentration). The positive control used was 10 µM hymenialdisine (final concentration) in a final vehicle concentration of 1% DMSO.

Reactions were initiated with the addition of ATP and allowed to proceed for 10 minutes at room temperature. The reactions were stopped by washing the plate five times with 300 µl/well of PBS. The plate was then counted on a Packard Top-Count.

CDK1/cyclinB1 was inhibited in a concentration-dependent manner by SCY. As shown in FIG. 7, SCY had an $IC_{50}$ of about 3 µM.

EXAMPLE 4

GST-Tie Kinase Activity Assay

To determine the effect of SCY on GST-Tie kinase activity, the following assay was conducted. Clones for the Tie2 receptor were obtained and submitted for confirmatory sequence analysis. Similar to the method described by Huang et al. (1995) Oncogene 11:2097–2103, which is herein incorporated by reference, GST fusion constructs using the human Tie kinase domains and the commercially available pAcG1 vector (Pharmigen, San Diego, Calif.) were constructed. In these constucts, the entire GST (*S. japonicum*) coding region is fused to the baculovirus polyhedron promoter with an EcoRI possessing polylinker replacing the stop codon for GST. A partial Tie2 cDNA clone was used, which already possessed an in-frame MunI site to fuse the kinase domain in frame to the EcoRI site. The desired restriction fragment was recovered from a partial Tie2 cDNA clone and then subcloned directly into the EcoRI site of the commercially pAcG1 expression vector. These final constructs were transfected into the baculovirus and GST-Tie2 kinase was semipurified using a glutathione affinity column to greater than about 90% purity, as determined via SDS-PAGE analysis and Coomassie Blue staining.

The kinase assay is carried out in 96 well flashplates and in the same kinase buffer used in the PLK1 kinase assays. Each reaction comprised 5 µg GST-Tie2 (intracellular kinase domain), 1 µCi $[^{33}\text{P}]$-ATP, 30 µM cold ATP in 60 µl. Compounds were in DMSO to give a final concentration of 1% DMSO. The reaction was incubated for 2 hours at 30° C. and terminated by washing the plate five times with 10 µM cold ATP. Reactions were quantitated by using a Packard Top-Count.

As shown in FIG. 7, SCY did not significantly affect or inhibit the activity of GST-Tie2 until concentrations of equal to or greater than about 10 µM of SCY were reached.

EXAMPLE 5

GST-Chk1 Activity Assay

To determine the effect of SCY on GST-Chk1 activity, the following assay was conducted. GST-Chk1 were expressed and purified using a method previously described in Jackson et al (2000) Can. Res. 60:566–572, which is herein incorporated by reference. GST-Chk1 was purified to 68% purity as determined via SDS-PAGE analysis. The remaining 30% was attributed to free GST. Flashplates were coated with 1 µg GST-cdc25C and 100 µM ATP at 4° C. The plates were washed twice with PBS, then 0.5 µCi $[^{33}\text{P}]$-γATP, 10 µM cold ATP, and 2 µg GST-CHK1 were added to the wells in kinase reaction buffer comprising 20 mM HEPES (pH 7.4), 50 mM KCl, 10 mM $MgCl_2$, 1 mM EGTA, and 0.5 mM DTT. Activity was measured in the presence of scytonemin (SCY) in 100% DMSO yielding a 4% DMSO final concentration. Reactions were initiated by the addition of the enzyme, incubated at 37° C. for 30 minutes, and stopped by washing the plates five times with PBS. The amount of $[^{33}\text{P}]$-γATP incorporation was measured on a Packard Topcount.

GST-CHK1 was inhibited in a concentration-dependent manner by SCY. As illustrated in FIG. 7, SCY had an $IC_{50}$ of about 1.4 µM.

EXAMPLE 6

PKC and PKA Activity Assays

RhPKCβ2 was expressed in a baculovirus expression system. Kinase reactions were conducted in 50 µl comprising 0.5 µg rhPKC diluted in 2 mM Tris, and 100 µM EGTA and reaction buffer comprising substrate (0.9 mM EGTA, 1.1 mM $CaCl_2$, 0.01 mg/ml glycogen synthase peptide (H-Pro-Leu-Ser-Arg-Thr-Leu-Ser-Val-Ala-Lys-Lys-OH) (Bachem, King of Prussia, Pa.), 40 µg/ml L-α-Phosphatidyl-L-serine, 1 µg/ml 1,3-Diolen, 10 mM $MgCl_2$, pH 7.5). To assess PKA activity, kinase reactions were conducted in 50 µl comprising 0.5 µg PKA (from bovine heart supplied by Sigma, St. Louis, Mo.) diluted in 10 mM MOPS, pH 6.5 and reaction buffer comprising substrate (50 mM MOPS, pH 6.5, 10 mM $MgCl_2$, 0.1 mg/ml Histone-IIA (Sigma, St. Louis, Mo.), 1 µM cAMP). An ATP solution (0.01 µM ATP and 0.5 µCi of $[\gamma^{33}\text{-P}]$ ATP) was then added to the wells in both assay systems. Inhibitors were added at the indicated concentrations with a final DMSO concentration of 10%. Reactions were allowed to proceed for 20 minutes at 37° C. and were stopped with 25 mM EDTA. The reactions were spotted onto filter paper, washed four times in a beaker comprising 75 mM phosphoric acid and rinsed with acetone. Filters were dried and put in scintillation vials with fluid and counted.

As shown in FIG. 7, SCY did not significantly affect or inhibit the activity of PKA until concentrations of equal to or greater than about 10 µM of SCY were reached. SCY did, however, inhibit rhPKC activity in a concentration-dependent manner showing an $IC_{50}$ of about 3 µM.

EXAMPLE 7

$[^3\text{H}]$-Thymidine Incorporation Assay

To determine the effect of SCY on the proliferation of several cell types, proliferation was measured in response to growth factor or serum by tritiated thymidine uptake. Rheumatoid synovial fibroblasts (RSFs) obtained from Dr. Gene Mochan at PCOM (Philadelphia, Pa.), normal human lung fibroblasts (NHLFs) (Clonetics, San Diego, Calif.), human umbilical vein endothelial cells (HUVECs) (Clonetics, San Diego, Calif.), and Jurkat T cells (ATCC, Rockville, Md.) were plated in 96 well cell culture plates (Falcon, Franklin Lakes, N.J.). About $1.2 \times 10^4$ RSF cells/well and about $1 \times 10^4$ NHLF cells/well were plated in EMEM (Eagle's Minimum Essential Medium) (Sigma, St. Louis, Mo.) comprising 10 units penicillin-streptomycin (penstrep) (GibcoBRL, Grand Island, New York) and 10% FBS. About $5 \times 10^3$ HUVEC cells/well were plated in CSC media (Cell Systems, Seattle, Wash.) with 10% FBS. Fibroblasts were allowed to adhere for about 6 to about 24 hours at 37° C., 5% $CO_2$ and the media was changed to EMEM or CSC, 0.2% FBS and incubated for 24 hours. About $2 \times 10^4$ Jurkat T cells/well (ATCC, Rockville, Md.) were plated in RPMI (Gibco BRL, Grand Island, N.Y.), comprising 10% FBS and 10 units penstrep.

All cells were incubated with compound or vehicle (0.5% DMSO) for 15 minutes at room temperature. RSFs were stimulated with 1 nM PDGF-BB, NHLFs with 5% FBS, and HUVECs with 0.5 μg/ml ECGF for 24 hours, then pulsed with 0.5 μCi/well [$^3$H]-thymidine (Amersham, Buckinghamshire, England), incubated for an additional 24 hours and harvested. Jurkats were pulsed immediately after plating cells and treating the cells with compound and then harvested about 24 to about 48 hours later. All the cells were harvested onto 96 well GF/C filtration plates (Packard, Meriden, Conn.) using a Packard microplate cell harvester (Packard). [$^3$H]-thymidine incorporation into the DNA was measured on a Packard Top-Count.

Figure 5A:
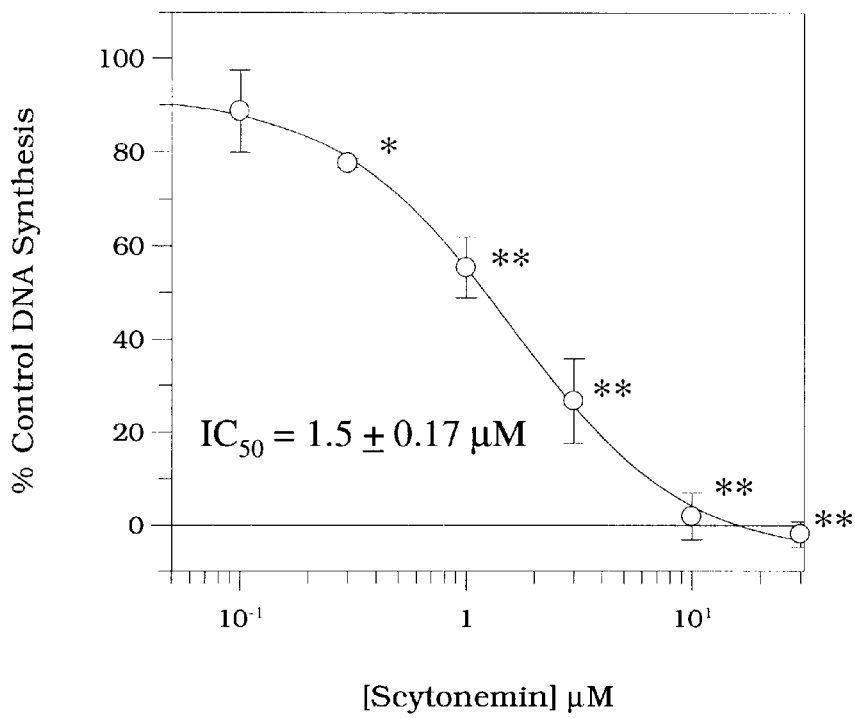
FIGS. 5a–d show that scytonemin inhibits growth factor-induced cell proliferation in the following cell types: (a) PDGF-BB stimulated rheumatoid synovial fibroblasts, (b) FBS-stimulated NHLFs, (c) endothelin growth supplement-induced HUVECs, and (d) FBS-stimulated Jurkats. Data presented as the % of tritiated-thymidine incorporated compared to the level observed in the vehicle (0.5% DMSO) controls for each cell type. Error bars represent standard deviation; *p<0.05; ** p<0.01; All $IC_{50}$ values given as $IC_{50}$±S.E.M.
Figure 5B:
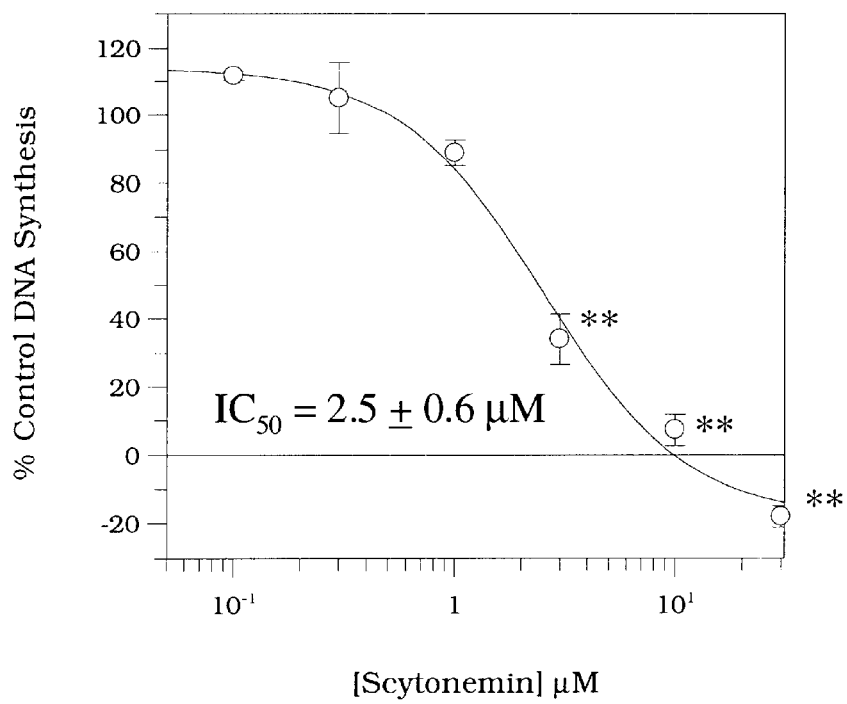
Figure 5C:
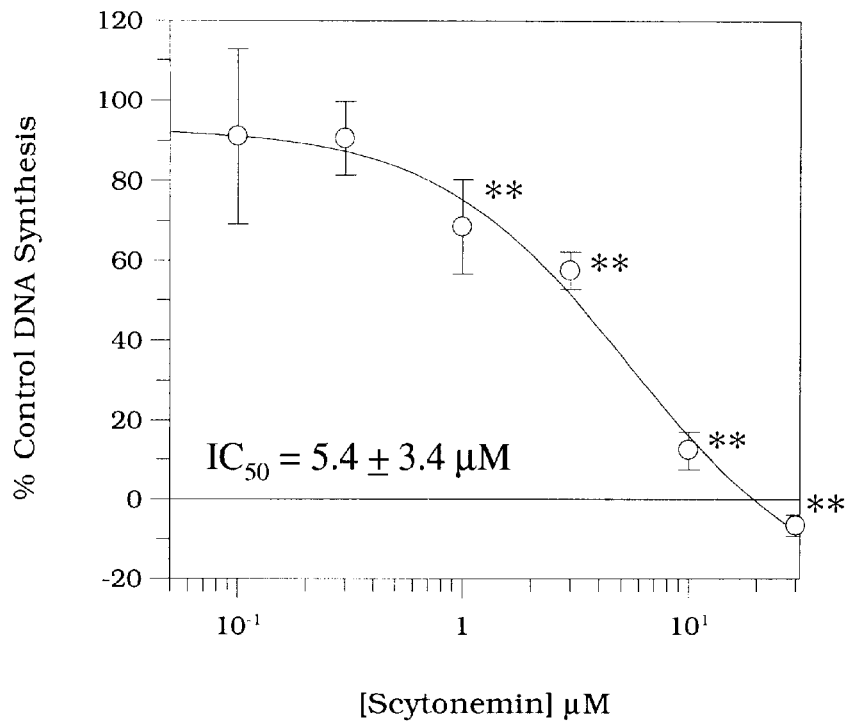
Figure 5D:
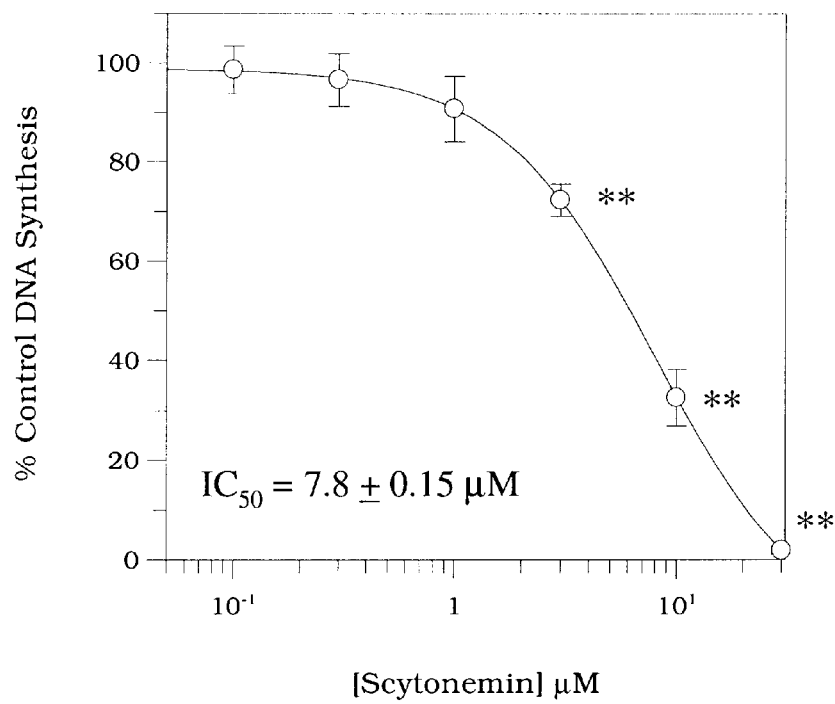

As shown in FIG. 5a, rheumatoid synovial fibroblast proliferation induced by platelet-derived growth factor was concentration-dependently inhibited by SCY with $IC_{50}$ of about 1.5 μM. FIG. 5b shows that endothelial cell growth factor-induced HUVEC proliferation was also concentration-dependently inhibited by SCY with $IC_{50}$ of about 2.5 μM. FIG. 5c shows that SCY also inhibited normal human lung fibroblast proliferation stimulated by fetal bovine serum in a concentration-dependent manner with $IC_{50}$ of about 2 μM to about 9 μM. As shown in FIG. 5d, Jurkat T cells, a perpetually proliferating cell line in the presence of serum, were inhibited in a concentration-dependent manner with $IC_{50}$ of about 7.8 μM.

Thus, SCY significantly reduced the level of DNA synthesis in each cell type in a concentration dependent manner.

EXAMPLE 8

Apoptosis Assay

To determine the mechanism behind the ability of SCY to inhibit cell proliferation, about $2 \times 10^5$ Jurkat T cells/ml were treated with vehicle (negative control), 3 μM SCY, or 3 μM camptothecin (positive control) a (0.1% $DMSO_{[final]}$) and incubated at 37° C., 5% $CO_2$ for 24 hours. As a positive control, camptothecin, a DNA topoisomerase inhibitor, was used because of its ability to arrest Jurkat cells at the G2/M phase of the cell cycle and induce the cells to undergo apoptosis. The cells were fixed in 1% paraformaldehyde, washed once with PBS, and stored in 70% EtOH at −20° C. Apoptosis was measured using the Promega Apoptosis Detection System (Promega, Madison, Wis.) an adapted TUNEL staining method.

The cells were washed two times with 5 ml PBS 2% FBS, then transferred to a microcentrifuge tube in 1 ml PBS, 0.2% TritonX100, 5 mg/ml BSA and incubated on ice for 5 minutes. Samples were spun, PBS solution removed, then resuspended in 80 μl equilibration buffer from Promega kit and incubated at room temperature for 10 minutes. Then the samples were spun and the equilibration buffer removed. A nucleotide mix comprising 45 μl equilibration buffer, 5 μl nucleotide mix, 1 μl Tdt enzyme per sample, was used to resuspend each sample in the dark. The cells were incubated in the dark at 37° C. for 1 hour. The reaction was terminated by the addition of 20 mM EDTA. The samples were washed twice with 1 ml RNAse A and a small aliquot, about 50 μl, was viewed under a microscope. Cells were stained with fluoroscein and then counterstained with propidium iodide and analyzed for DNA content and fragmentation using a Becton-Dickinson FacsSort (Becton-Dickinson, San Jose, Calif.).

Figure 6:
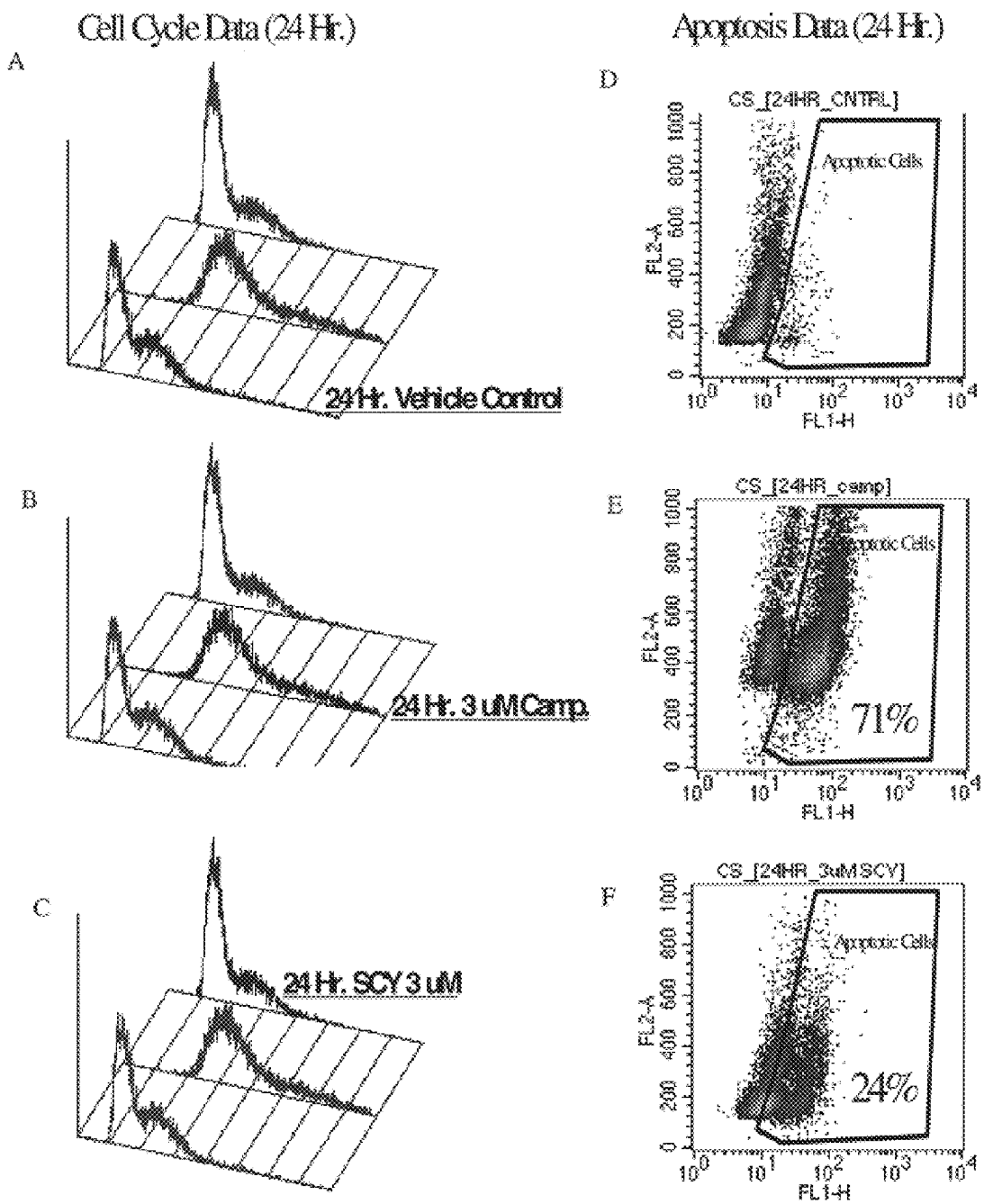
FIGS. 6A–6F Illustrate that scytonemin induces apoptosis in Jurkat T cells. The results were obtained using flow cytometric analysis. The effect the compound had on cell cycle progression is on the left and the level of DNA fragmentation is on the right.

FIGS. 6A and B show that the control population has cells distributed throughout the phases of the cell cycle and only a few cells with fragmented DNA. FIGS. 6C and D, show that 3 μM camptothecin arrested the cells at G2/M phase and induced 71% of the cells to undergo apoptosis. As shown in FIG. 6E, SCY did not have any cell cycle specific effect as did camptothecin, but it did cause the cells to undergo apoptosis in all phases of the cell cycle. See FIG. 6F.

Thus, scytoneman compounds may be used to induce apoptosis.

EXAMPLE 9

Anti-inflammatory Mouse Ear Assays

A. Inhibition of Mouse Ear Edema.

The efficacy of a scytoneman compound as an anti-inflammatory agent may be established by the following assay. The scytoneman compound is topically applied in acetone to the inside pinnae of the ears of mice in a solution comprising an irritant such as the edema-causing irritant, Phorbol 12-myristate 13-acetate (PMA). Specifically, 2 μg/ear of PMA alone or in combination with 50 μg/ear of the test compound, scytonemin, was applied to the left ears (5 mice per treatment group) and acetone was applied to all right ears. After 3 hours, 20 minutes incubation, the mice were sacrificed, the ears removed and bores taken and weighed. Edema was measured by subtracting the weight of the right ear (acetone control) from the weight of the left ear (treated). Results were recorded as % decrease (inhibition) or % increase (potentiation) in edema relative to the PMA control group edema.

B. Myeloperoxidase (MPO) Enzyme Assay.

To determine neutrophil influx into inflamed tissue region, the following assay may be conducted. Generally, myeloperoxidase (MPO), a neutrophil-specific marker released from primary granules, is indicative of the extravasation of pro-inflammation neutrophils from blood into the skin. Thus, to determine whether a test compound prevents, inhibits, modulates or attenuates inflammation related to an immunogenic inflammatory pathway or neutrophil influx, ear biopsies from treated and untreated mouse ears may be extracted and quantitated according to a modified method of Bradley, P.O., et al. (1982) J. Invest Dermatology 78:206–209, which is herein incorporated by reference. Specifically, ear bores from each treatment group from mouse ear edema assays from part A above were pooled and homogenized in 80 mM sodium phosphate buffer (pH 5.4) comprising 0.5% hexadecyltrimethylammonium bromide in a siliconized glass test tube for 1 minute at 0° C. using a Brinkman Polytron. The mixtures were centrifuged at 10,000×g at 4° C. for 30 minutes. 10 μl samples from each group were then assayed in a 96-well microtiter plate. The assay was initiated by adding 250 µl of o-dianisi-dine/phosphate reagent (0.28 mg of dianisidine added to 1 ml of 50 mM sodium phosphate comprising 0.0015 $H_2O_2$) to each well. After a 30 minute incubation at 37° C., the plates were read at 450 nm on a Molecular Devices microplate reader. Diluted control biopsies were utilized to develop a standard curve. Optical density values from drug-treated groups were compared to control groups to determine the % of control values of enzyme activity.

Figure 8:
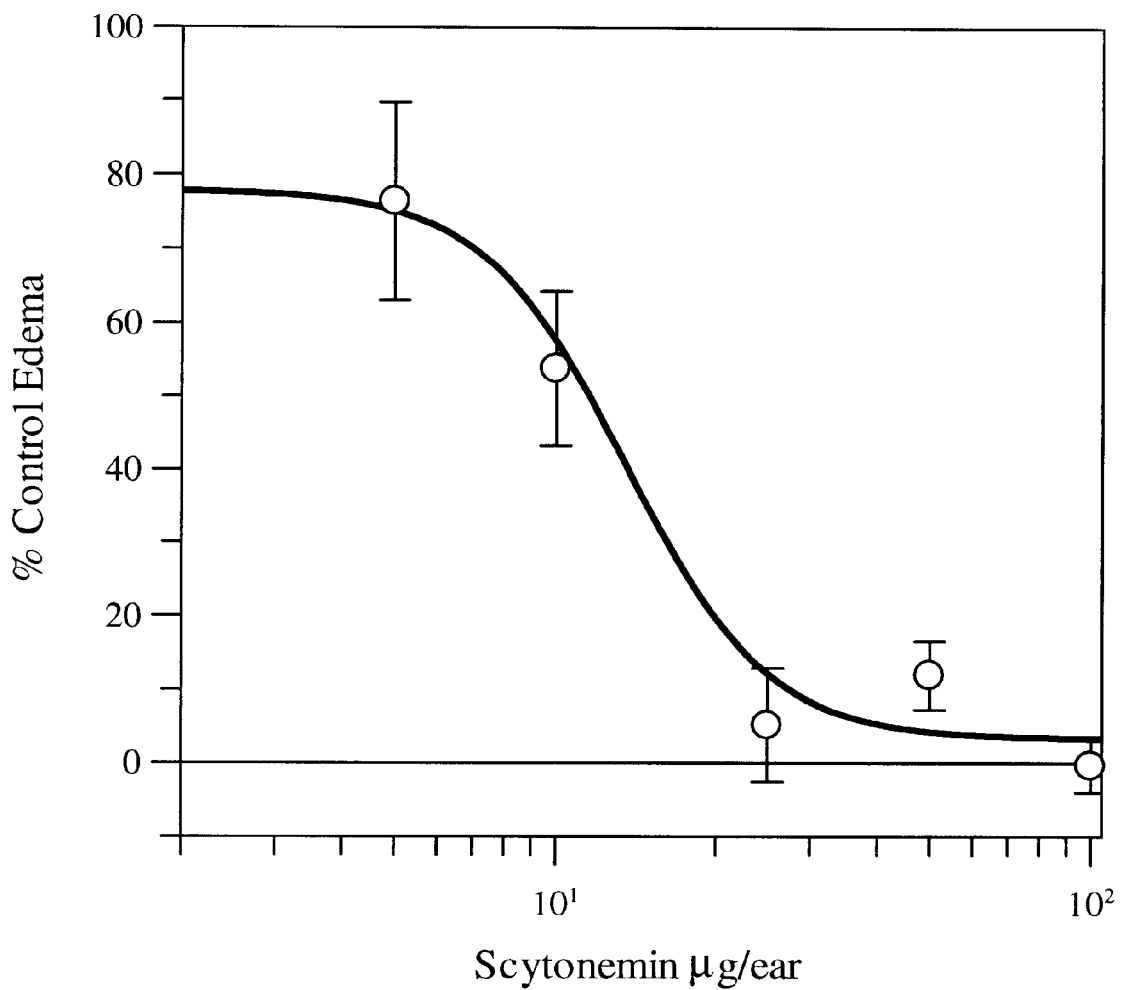
FIG. 8 shows that topical application of scytonemin prevents PMA-induced mouse ear edema and tissue MPO activity. Error bars represent standard deviation; *p<0.05; **p<0.01; All $IC_{50}$ values given as $IC_{50}$±S.E.M.

As shown in FIG. 8, topical application of scytonemin prevents PMA-induced mouse ear edema and tissue myeloperoxidase activity with an $ED_{50}$ of about 10.9±5 µg per ear. Specifically, 1, 5, 10 and 100 µg of scytonemin inhibited MPO activity by about 19%, 18%, 68% and 90%, respectively. Thus, a scytoneman compound such as scytonemin may be used to treat, prevent, or inhibit inflammation relating to an immunogenic inflammatory pathway or neutrophil influx.

EXAMPLE 10

Resiniferatoxin (RTX) and Capsaicin (CAP) Assay

Various dilutions of test compounds were topically applied in acetone to the inside and outside surfaces of the left ears of mice in a solution comprising 0.1 µg RTX or 250 µg CAP per ear. A control, acetone, was applied to all right ears. After a 30 minute incubation, the mice were sacrificed, the ears removed, and bores taken and weighed.

For systemic studies, the test compounds were administered by intraperitoneal injection in a vehicle comprising 20% propylene glycol, 80% saline and 3 drops TWEEN-20 30 minutes or 1 hour prior to topical application of RTX or CAP. Control animals were injected with vehicle only. 0.1 µg RTX or 250 µg CAP was applied to the left ears and acetone was applied to the right ears. After 30 minutes of incubation, the mice were scarified, ears removed and bores taken and weighed.

Edema was measured by subtracting the weight of the right ear (control) from the weight of the left ear. The results were recorded as % decrease (inhibition) or % increase (potentiation) in edema relative to the control group edema.

When topically applied and screened at 500 µg/ear against 250 µg/ear CAP, scytonemin showed about a 24% inhibition of edema. Scytonemin displayed concentration dependent inhibition of RTX-induced mouse ear edema with an $ED_{50}$ of about 15 µg/ear. The $ED_{50}$ value, about 10 µg/ear, for scytonemin was similar to the $ED_{50}$ obtained in the PMA-induced model, about 12 µg/ear.

When given systemically at 10 mg/kg 30 minutes before topical CAP, scytonemin showed no inhibition of edema. However, scytonemin showed a concentration-dependent inhibition of topical RTX-induced mouse ear edema with 47% inhibition at 150 mg/kg, 18% inhibition at 50 mg/kg, and 15% inhibition at 25 mg/kg.

Thus, scytoneman compounds may be used to treat, prevent, or inhibit inflammation relating to a neurogenic inflammatory pathway.

EXAMPLE 11

Mouse Ear Cell Proliferation Assay

To determine the efficacy of scytonemin as an antiproliferative agent in vivo, the following assay was conducted. On day one, test compounds were delivered in 10 µl 20% DMSO, 80% acetone and applied to both the inner and outer pinnae of left ears (20 µl total) of male, Swiss Webster mice (Taconic Farms, Germantown, N.Y.). The right ears received only vehicle. One hour post test compound application, 4 µg/ear PMA (Sigma, St. Louis, Mo.) in 10 µl acetone was applied to the inner pinnae of each left ear and 10 µl acetone was applied to each right ear. Four hours post test compound application, the each test compound was again applied in the same manner. On day two, the test compounds were applied twice with a four-hour interval between each application. On day three, the test compounds and PMA were applied as they had been on day one. One hour after the final test compound applications, each mouse was injected with 0.6 ml of a solution containing the thymidine analogue, 5-iodo-$I^{125}$-2'-deoxyuridine (IUdR) (2 µCi-$I^{125}$/mouse) and, to inhibit the endogenous deoxythymidilic acid synthetase, fluorodeoxyuridine (FUdR) (15.6 mg/mice). This IUdR/FUdR solution was made up in RPMI 1640 media. Eighteen hours post injection, the mice were euthanized via $CO_2$ inhalation, the ears were excised and soaked individually in a 70% EtOH solution overnight.

IUdR incorporation was then measured using a Beckman Gamma counter, Model 5500B. Dexamethasone (0.2 mg/ear) was used as a positive control. As illustrated in FIG. 9, scytonemin effectively reduced or prevented cell proliferation in vivo. Therefore, scytoneman compounds may be used to reduce, prevent, inhibit, modulate, or attenuate cell proliferation.

Incorporation by Reference

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A method of inhibiting, modulating, or attenuating cell-cycle progression, intracellular signaling, or cell proliferation of a cell comprising exposing the cell to at least one scytoneman compound.

2. The method of claim 1, wherein the scytoneman compound is scytonemin.

3. A method of inhibiting, modulating, attenuating, or preventing a kinase, kinase activity, or phosphorylation of a substrate by a kinase comprising exposing the kinase to at least one scytoneman compound.

4. The method of claim 3, wherein the kinase is a cell cycle regulatory kinase or an intracellular signaling kinase.

5. The method of claim 3, wherein the kinase is a serine/threonine kinase, a threonine/tyrosine kinase, or a tyrosine kinase.

6. The method of claim 3, wherein the kinase is a polo-like kinase, a cyclin-dependent kinase, or a checkpoint kinase.

7. The method of claim 3, wherein the kinase is PLK1, Myt1, CHK1, CDK1/cyclinB, PKCβ2, PKA, or Tie2.

8. A method of treating or inhibiting a disease or disorder associated with cell cycle progression, cell proliferation, kinase activity, tissue hyperplasia or angiogenesis in a subject comprising administering at least one scytoneman compound to the subject.

9. The method of claim 8, wherein the subject is a mammal.

10. The method of claim 9, wherein the mammal is human.

11. The method of claim 8, wherein the disease or disorder is an acute or a chronic inflammatory disease or disorder.

12. The method of claim 8, wherein the disease or disorder is cancer, a papilloma, rheumatoid arthritis, psoriasis, atherosclerosis, diabetic retinopathy, chronic obstructive pulmonary disorder, tuberculosis, chronic cholecystitis, osteoarthritis, rheumatic carditis, bronchiectasis, Hashimoto's thyroiditis, ulcerative colitis, Crohn's disease, or silicosis.

13. The method of claim 8, wherein the disease or disorder is cancer, rheumatoid arthritis, angiogenesis, or psoriasis.

14. The method of claim 8, wherein the scytoneman compound is administered in a therapeutically effective amount or concentration.

15. A method of inducing apoptosis in a cell comprising exposing the cell to at least one scytoneman compound.

16. A method of treating a disease, disorder, or tissue, in a subject comprising inducing apoptosis in a target by administering at least one scytonemin compound to the subject.

17. The method of claim 16, wherein the target is a cell, an abnormal cell, or an organism.

* * * * *